US011944531B2

(12) United States Patent
Kubiak et al.

(10) Patent No.: US 11,944,531 B2
(45) Date of Patent: Apr. 2, 2024

(54) DEVICES, SYSTEMS, AND METHODS FOR REPAIRING SOFT TISSUE AND ATTACHING SOFT TISSUE TO BONE

(71) Applicant: CONEXTIONS, INC., Salt Lake City, UT (US)

(72) Inventors: Erik N. Kubiak, Las Vegas, NV (US); Roy M. Taylor, Salt Lake City, UT (US); Zackery K. Evans, Woods Cross, UT (US); Cody L. Gehrke, South Jordan, UT (US); Daniel K. Smith, Woods Cross, UT (US); Richard J. Linder, Sandy, UT (US); Scott D. Miles, Sandy, UT (US); Tyler J. Cole, Sandy, UT (US)

(73) Assignee: CONEXTIONS, INC., Salt Lake City, UT (US)

( * ) Notice: Subject to any disclaimer, the term of this patent is extended or adjusted under 35 U.S.C. 154(b) by 257 days.

(21) Appl. No.: 15/870,447

(22) Filed: Jan. 12, 2018

(65) Prior Publication Data

US 2018/0200042 A1   Jul. 19, 2018

Related U.S. Application Data

(63) Continuation-in-part of application No. 15/719,346, filed on Sep. 28, 2017, now Pat. No. 10,835,241, (Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/064* (2013.01);
(Continued)

(58) Field of Classification Search
CPC ... A61B 17/04; A61B 17/08; A61B 17/07292; A61B 17/064; A61B 17/0686;
(Continued)

(56) References Cited

U.S. PATENT DOCUMENTS

| 3,166,072 A | 1/1965 | Sullivan et al. |
| 4,388,926 A | 6/1983 | Shalaby et al. |

(Continued)

FOREIGN PATENT DOCUMENTS

| CN | 104023649 | 9/2014 |
| JP | 2006503655 | 2/2006 |

(Continued)

OTHER PUBLICATIONS

McKenzie, "An Experimental Multiple Barbed Suture for the Long Flexor Tendons of The Palm and Fingers," Journal of Bone and Joint Surgery, Aug. 1967, pp. 440-447, vol. 49 B, No. 3.

(Continued)

*Primary Examiner* — Jerrah Edwards
*Assistant Examiner* — Christine L Nelson
(74) *Attorney, Agent, or Firm* — David L. Stott

(57) ABSTRACT

Devices, systems and/or methods for repairing soft tissue adjacent a soft tissue repair site. In one embodiment, a repair device configured to couple to soft tissue is provided. The repair device includes a capture portion and an anchor portion. The capture portion configured to extend with radial portions. The anchor portion includes a base with multiple legs extending therefrom. The multiple legs are configured to move from a linear position to a formed position such that, in the formed position, the multiple legs couple to structure of the capture portion.

23 Claims, 17 Drawing Sheets

Related U.S. Application Data which is a continuation-in-part of application No. 14/885,959, filed on Oct. 16, 2015, now Pat. No. 10,219,804, which is a continuation-in-part of application No. 14/645,924, filed on Mar. 12, 2015, now Pat. No. 9,629,632, which is a continuation-in-part of application No. 13/953,709, filed on Jul. 29, 2013, now Pat. No. 9,427,309.

(60) Provisional application No. 62/581,031, filed on Nov. 2, 2017, provisional application No. 62/464,300, filed on Feb. 27, 2017, provisional application No. 62/445,596, filed on Jan. 12, 2017, provisional application No. 62/401,042, filed on Sep. 28, 2016, provisional application No. 62/215,739, filed on Sep. 9, 2015, provisional application No. 62/129,742, filed on Mar. 6, 2015, provisional application No. 62/094,032, filed on Dec. 18, 2014, provisional application No. 62/064,533, filed on Oct. 16, 2014, provisional application No. 62/053,056, filed on Sep. 19, 2014, provisional application No. 62/040,451, filed on Aug. 22, 2014, provisional application No. 62/007,783, filed on Jun. 4, 2014, provisional application No. 61/952,114, filed on Mar. 12, 2014, provisional application No. 61/804,570, filed on Mar. 22, 2013, provisional application No. 61/677,239, filed on Jul. 30, 2012.

(51) Int. Cl.
*A61B 17/064* (2006.01)
*A61B 17/068* (2006.01)
*A61B 17/072* (2006.01)
*A61B 17/10* (2006.01)
*A61B 17/11* (2006.01)
*A61B 17/115* (2006.01)
*A61B 17/00* (2006.01)

(52) U.S. Cl.
CPC ........ *A61B 17/0686* (2013.01); *A61B 17/072* (2013.01); *A61B 17/105* (2013.01); *A61B 17/1146* (2013.01); *A61B 17/115* (2013.01); *A61F 2/0805* (2013.01); *A61B 2017/00867* (2013.01); *A61B 2017/0414* (2013.01); *A61B 2017/0464* (2013.01); *A61B 17/0466* (2013.01); *A61B 17/0487* (2013.01); *A61B 2017/0641* (2013.01); *A61B 17/0643* (2013.01); *A61B 17/0644* (2013.01); *A61B 2017/0645* (2013.01); *A61B 2017/1103* (2013.01); *A61B 2017/1132* (2013.01); *A61F 2002/0823* (2013.01); *A61F 2002/0835* (2013.01); *A61F 2002/0852* (2013.01)

(58) Field of Classification Search
CPC . A61B 17/105; A61B 17/1146; A61B 17/115; A61B 17/0643; A61B 2017/0464; A61B 2017/0641; A61B 2017/0645; A61F 2/0811; A61F 2/0805; A61F 2002/0852
See application file for complete search history.

(56) References Cited

U.S. PATENT DOCUMENTS

| | | | |
|---|---|---|---|
| 4,414,967 A | 11/1983 | Shapiro | |
| 4,454,875 A | 6/1984 | Pratt et al. | |
| 4,461,298 A | 7/1984 | Shalaby et al. | |
| 4,469,101 A | 9/1984 | Coleman et al. | |
| 4,489,875 A | 12/1984 | Crawford et al. | |
| 4,532,926 A | 8/1985 | O'Holla | |
| 4,534,350 A | 8/1985 | Golden et al. | |
| 4,548,202 A | 10/1985 | Duncan | |
| 4,610,250 A * | 9/1986 | Green | A61B 17/0643 411/450 |
| 4,655,222 A | 4/1987 | Florez et al. | |
| 4,655,980 A | 4/1987 | Chu | |
| 4,741,330 A | 5/1988 | Hayhurst | |
| 4,776,890 A | 10/1988 | Chu | |
| 4,796,612 A | 1/1989 | Reese | |
| 4,810,549 A | 3/1989 | Abrams et al. | |
| 4,873,976 A | 10/1989 | Schreiber | |
| 4,942,875 A | 7/1990 | Hlavacek et al. | |
| 4,946,467 A | 8/1990 | Ohi et al. | |
| 4,960,420 A | 10/1990 | Goble et al. | |
| 4,983,184 A | 1/1991 | Steinemann | |
| 5,047,103 A | 9/1991 | Abrams et al. | |
| 5,061,283 A | 10/1991 | Silvestrini | |
| 5,163,956 A | 11/1992 | Liu et al. | |
| 5,207,841 A | 5/1993 | Abrams | |
| 5,209,756 A * | 5/1993 | Seedhom | A61B 17/88 606/220 |
| 5,250,049 A | 10/1993 | Michael | |
| 5,290,552 A | 3/1994 | Sierra et al. | |
| 5,292,334 A | 3/1994 | Howansky | |
| 5,306,290 A | 4/1994 | Martins et al. | |
| 5,306,500 A | 4/1994 | Rhee et al. | |
| 5,312,023 A | 5/1994 | Green et al. | |
| 5,326,013 A | 7/1994 | Green et al. | |
| 5,329,943 A | 7/1994 | Johnson | |
| 5,342,376 A | 8/1994 | Ruff | |
| 5,346,746 A | 9/1994 | Abrams | |
| 5,370,662 A | 12/1994 | Stone et al. | |
| 5,389,098 A | 2/1995 | Tsuruta et al. | |
| 5,413,791 A | 5/1995 | Rhee et al. | |
| 5,446,091 A | 8/1995 | Rhee et al. | |
| 5,447,265 A | 9/1995 | Vidal et al. | |
| 5,458,636 A | 10/1995 | Brancato | |
| 5,465,894 A | 11/1995 | Clark et al. | |
| 5,480,644 A | 1/1996 | Freed | |
| 5,510,418 A | 4/1996 | Rhee et al. | |
| 5,523,348 A | 6/1996 | Rhee et al. | |
| 5,527,341 A | 6/1996 | Gogolewski et al. | |
| 5,542,594 A | 8/1996 | McKean et al. | |
| 5,556,428 A | 9/1996 | Shah | |
| 5,575,803 A | 11/1996 | Cooper et al. | |
| 5,580,923 A | 12/1996 | Yeung et al. | |
| 5,597,637 A | 1/1997 | Abrams et al. | |
| 5,601,557 A | 2/1997 | Hayhurst | |
| 5,603,443 A | 2/1997 | Clark et al. | |
| 5,607,094 A | 3/1997 | Clark et al. | |
| 5,630,824 A | 5/1997 | Hart | |
| 5,630,842 A | 5/1997 | Brodniewicz | |
| 5,649,937 A | 7/1997 | Bito et al. | |
| 5,665,112 A | 9/1997 | Thal | |
| 5,667,839 A | 9/1997 | Berg | |
| 5,706,997 A | 1/1998 | Green et al. | |
| 5,711,472 A | 1/1998 | Bryan | |
| 5,713,903 A | 2/1998 | Sander et al. | |
| 5,716,981 A | 2/1998 | Hunter et al. | |
| 5,723,008 A | 3/1998 | Gordon | |
| 5,728,110 A | 3/1998 | Vidal et al. | |
| 5,732,871 A | 3/1998 | Clark et al. | |
| 5,756,678 A | 5/1998 | Shenoy et al. | |
| 5,766,250 A | 6/1998 | Chervitz et al. | |
| 5,785,713 A | 7/1998 | Jobe | |
| 5,800,544 A | 9/1998 | Demopulos et al. | |
| 5,807,581 A | 9/1998 | Rosenblatt et al. | |
| 5,840,078 A | 11/1998 | Yerys | |
| 5,858,156 A | 1/1999 | Abrams et al. | |
| 5,860,229 A | 1/1999 | Morgenstern | |
| 5,865,361 A | 2/1999 | Milliman et al. | |
| 5,908,427 A | 6/1999 | McKean et al. | |
| 5,916,224 A | 6/1999 | Esplin | |
| 5,947,999 A | 9/1999 | Groiso | |
| 5,961,520 A | 10/1999 | Beck, Jr. et al. | |
| 5,964,774 A | 10/1999 | McKean et al. | |
| 5,980,524 A | 11/1999 | Justin et al. | |
| 5,997,811 A | 12/1999 | Esposito | |
| 6,010,764 A | 1/2000 | Abrams | |

(56) References Cited

U.S. PATENT DOCUMENTS

| | | |
|---|---|---|
| 6,013,083 A | 1/2000 | Bennett |
| 6,027,523 A | 2/2000 | Schmieding |
| 6,030,410 A | 2/2000 | Zurbrugg |
| 6,045,560 A | 4/2000 | McKean et al. |
| 6,079,606 A | 6/2000 | Milliman et al. |
| 6,080,192 A | 6/2000 | Demopulos et al. |
| 6,083,242 A | 7/2000 | Cook |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,206,886 B1 | 3/2001 | Bennett |
| 6,241,139 B1 | 6/2001 | Milliman et al. |
| 6,241,747 B1 | 6/2001 | Ruff |
| 6,250,532 B1 | 6/2001 | Green et al. |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,464,706 B1 | 10/2002 | Winters |
| 6,472,171 B1 | 10/2002 | Toman et al. |
| 6,485,503 B2 | 11/2002 | Jacobs et al. |
| 6,491,714 B1 | 12/2002 | Bennett |
| 6,495,127 B1 | 12/2002 | Wallace et al. |
| 6,515,016 B2 | 2/2003 | Hunter |
| 6,517,579 B1 | 2/2003 | Paulos et al. |
| 6,533,802 B2 | 3/2003 | Bojarski et al. |
| 6,544,273 B1 | 4/2003 | Harari et al. |
| 6,551,315 B2 | 4/2003 | Kortenbach et al. |
| 6,569,186 B1 | 5/2003 | Winters et al. |
| 6,575,976 B2 | 6/2003 | Grafton |
| 6,644,532 B2 | 11/2003 | Green et al. |
| 6,645,226 B1 | 11/2003 | Jacobs et al. |
| 6,648,893 B2 | 11/2003 | Dudasik |
| 6,652,563 B2 | 11/2003 | Dreyfuss |
| 6,656,183 B2 | 12/2003 | Colleran et al. |
| 6,656,215 B1 | 12/2003 | Yanez et al. |
| 6,666,873 B1 | 12/2003 | Cassell |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,233 B1 | 6/2004 | Baldwin et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,905,513 B1 | 6/2005 | Metzger |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,074,203 B1 | 7/2006 | Johanson et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,189,238 B2 | 3/2007 | Lombardo et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,275,674 B2 * | 10/2007 | Racenet ............... A61B 17/072 227/176.1 |
| 7,296,724 B2 | 11/2007 | Green et al. |
| 7,303,107 B2 | 12/2007 | Milliman et al. |
| 7,303,577 B1 | 12/2007 | Dean |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,442,202 B2 | 10/2008 | Dreyfuss |
| 7,464,848 B2 | 12/2008 | Green et al. |
| 7,510,566 B2 | 3/2009 | Jacobs et al. |
| 7,530,484 B1 | 5/2009 | Durrani |
| 7,530,990 B2 | 5/2009 | Perriello et al. |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess et al. |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,635,367 B2 | 12/2009 | Groiso |
| 7,640,617 B2 | 1/2010 | Kennedy et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,731,718 B2 | 6/2010 | Schwammberger et al. |
| 7,771,468 B2 | 8/2010 | Whitbourne et al. |
| 7,794,484 B2 | 9/2010 | Stone et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,887,551 B2 | 2/2011 | Bojarski et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,057,524 B2 | 11/2011 | Meridew |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racen et al. |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |

(56) References Cited

U.S. PATENT DOCUMENTS

| | | |
|---|---|---|
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,343,186 B2 | 1/2013 | Dreyfuss et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,491,600 B2 | 7/2013 | McDevitt et al. |
| 8,500,776 B2 | 8/2013 | Ebner |
| 8,518,091 B2 | 8/2013 | McDevitt et al. |
| 8,540,131 B2 | 9/2013 | Swayze |
| 8,550,325 B2 | 10/2013 | Cohen et al. |
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |
| 8,840,003 B2 | 9/2014 | Morgan et al. |
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 10,299,842 B2 | 5/2019 | Hollis et al. |
| 10,835,241 B2 | 11/2020 | Kubiak et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0173807 A1 | 11/2002 | Jacobs |
| 2002/0192280 A1 | 12/2002 | Hunter et al. |
| 2003/0065360 A1 | 4/2003 | Jacobs et al. |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130735 A1 | 7/2003 | Rogalski |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0220616 A1 | 11/2004 | Bonutti et al. |
| 2004/0224023 A1 | 11/2004 | Hunter et al. |
| 2004/0254609 A1* | 12/2004 | Esplin ............... A61B 17/0401 606/232 |
| 2004/0260340 A1 | 12/2004 | Jacobs et al. |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0162022 A1 | 7/2007 | Zhang et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0020584 A1 | 1/2009 | Soltz et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0149884 A1 | 6/2009 | Snyder et al. |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Dean et al. |
| 2009/0280153 A1 | 11/2009 | Hunter et al. |
| 2009/0299386 A1 | 12/2009 | Meridew |
| 2009/0324720 A1 | 12/2009 | He et al. |
| 2010/0016872 A1 | 1/2010 | Bayton et al. |

(56) References Cited

U.S. PATENT DOCUMENTS

| | | |
|---|---|---|
| 2010/0023052 A1 | 1/2010 | Heinrich et al. |
| 2010/0160718 A1 | 6/2010 | Villafana et al. |
| 2010/0193568 A1 | 8/2010 | Scheib et al. |
| 2010/0198258 A1 | 8/2010 | Heaven et al. |
| 2010/0217314 A1 | 8/2010 | Holsten et al. |
| 2010/0228078 A1 | 9/2010 | Sater |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1* | 4/2012 | Shelton, IV .......... A61B 17/105 206/339 |
| 2012/0130374 A1 | 5/2012 | Bouduban et al. |
| 2012/0203253 A1 | 8/2012 | Kubiak |
| 2012/0245629 A1 | 9/2012 | Gross et al. |
| 2013/0131781 A1 | 5/2013 | Greenhalgh et al. |
| 2013/0144310 A1 | 6/2013 | Gordon et al. |
| 2013/0197580 A1 | 8/2013 | Perriello et al. |
| 2014/0039551 A1 | 2/2014 | Donahue |
| 2014/0067061 A1 | 3/2014 | Kubiak et al. |
| 2014/0214037 A1 | 7/2014 | Mayer et al. |
| 2015/0245841 A1 | 9/2015 | Linder et al. |
| 2015/0272567 A1 | 10/2015 | Feezor et al. |
| 2015/0289866 A1 | 10/2015 | Bowen et al. |
| 2016/0066900 A1 | 3/2016 | Brunsvold et al. |
| 2016/0066907 A1 | 3/2016 | Cheney et al. |
| 2016/0100835 A1 | 4/2016 | Linder et al. |
| 2016/0100933 A1 | 4/2016 | Linder et al. |
| 2016/0174965 A1 | 6/2016 | Brunsvold |
| 2016/0242771 A1 | 8/2016 | Weinstein et al. |
| 2017/0027578 A1 | 2/2017 | Friedman et al. |
| 2017/0056158 A1 | 3/2017 | Saing |
| 2017/0156847 A1 | 6/2017 | Ricci et al. |
| 2017/0333026 A1 | 11/2017 | Dreyfuss et al. |
| 2018/0078253 A1 | 3/2018 | Kubiak et al. |
| 2018/0200042 A1 | 7/2018 | Kubiak et al. |
| 2021/0100545 A1 | 4/2021 | Thies |

FOREIGN PATENT DOCUMENTS

| | | |
|---|---|---|
| WO | WO2004037094 | 5/2004 |
| WO | WO2016061530 | 4/2016 |
| WO | WO2016138033 | 9/2016 |
| WO | WO2019164853 | 8/2019 |

OTHER PUBLICATIONS

Momose et al., "Suture Techniques With High Breaking Strength and Low Gliding Resistance: Experiments in the Dog Flexor Digitorum Pofundus Tendon," Acta Orthop Scand, 2001, 72(6):635-641.

Leung et al., "Barbed, Bi-Directional Medical Sutures: Biomechanical Properties and Wound Closure Efficacy Study," Society for Biomaterials 28ths Annual Meeting Transactions, 2002, p. 724.

Chunfeng et al., "Enhancing The Strength of the Tendon-Suture Interface Using 1-Ethyl-3-(3-dimethylaminoproply) Carbodimide Hydrochloride and Cyanoacrylate," Journal of Hand Surger, 2007, 32(5): 606-11.

Burkhead et al., "Use of Graft Jacket as an Augmentation for Massive Rotator Cuff Tears," Semin Arthro, 2007, 18(1): 11-18.

Hirpara et al., "A Barbed Device for Digital Flexor Tendon Repair," http://proceedings.jbjs.org.uk/cgi/content/abstract/92-B/SUPP_II/291-d, Mar. 2010.

International Search Report dated May 8, 2019 for International Application No. PCT/US2019/018628 (14 pages).

Office Action issued in EP 15850646.9 dated Sep. 19, 2019.

Office Action with English Translation issued in CN 201580066314.4 dated Jun. 22, 2018.

Supplementary European Search Report issued in EP 15850646.9 dated Jun. 25, 2018.

International Search Report dated Feb. 26, 2016 for International Application No. PCT/US2015/56059 (14 pages).

International Search Report dated Jul. 20, 2015 for International Application No. PCT/US2015/020231 (10 pages).

International Search Report dated Oct. 10, 2013 for International Application No. PCT/US2013/052735 (7 pages).

Supplementary European Search Report dated Oct. 20, 2021 for European App. No. 19756761 (10 pages).

Office Action with English Translation in Japanese App. No. 2020-566536 dated Nov. 29, 2022 (7 pages).

Office Action in Chinese App. No. 201980014553.3 dated Feb. 10, 2023 (9 pages).

* cited by examiner

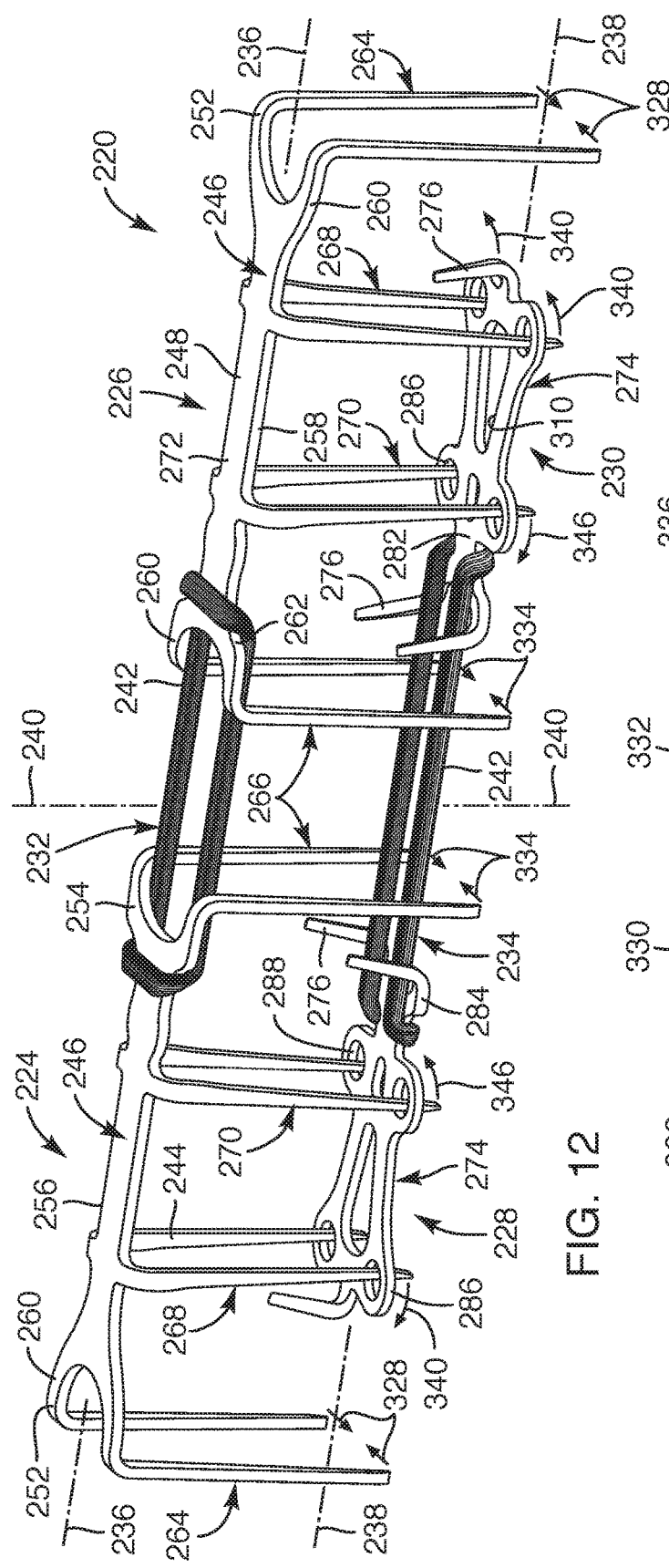
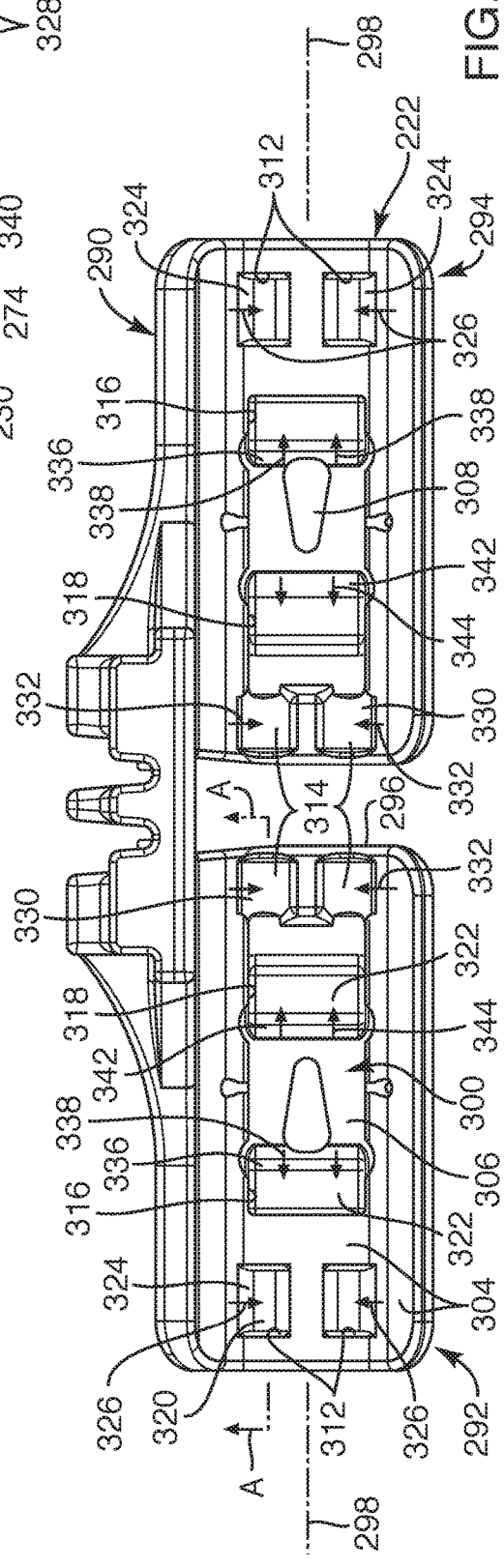
FIG. 12
FIG. 13

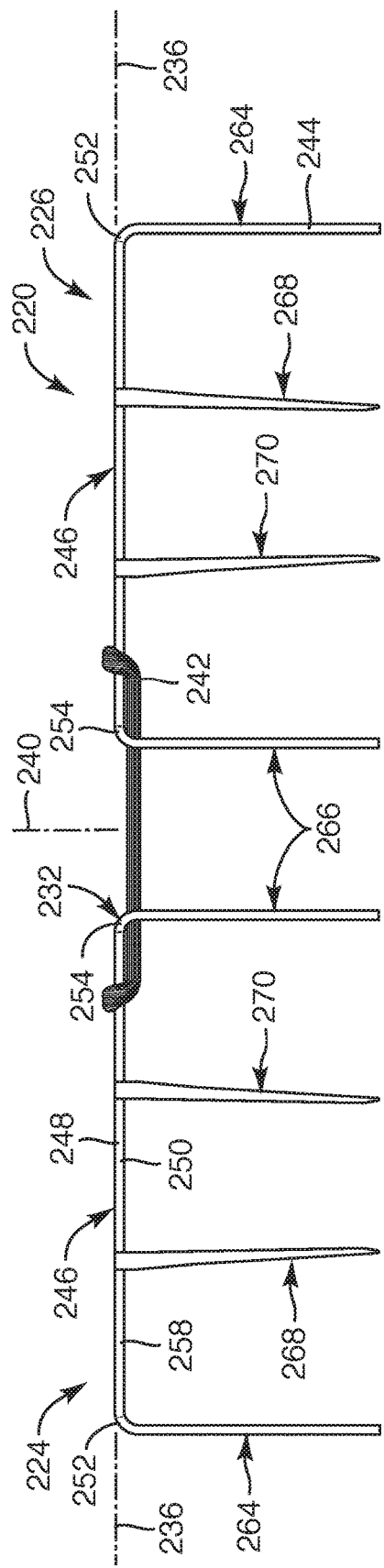
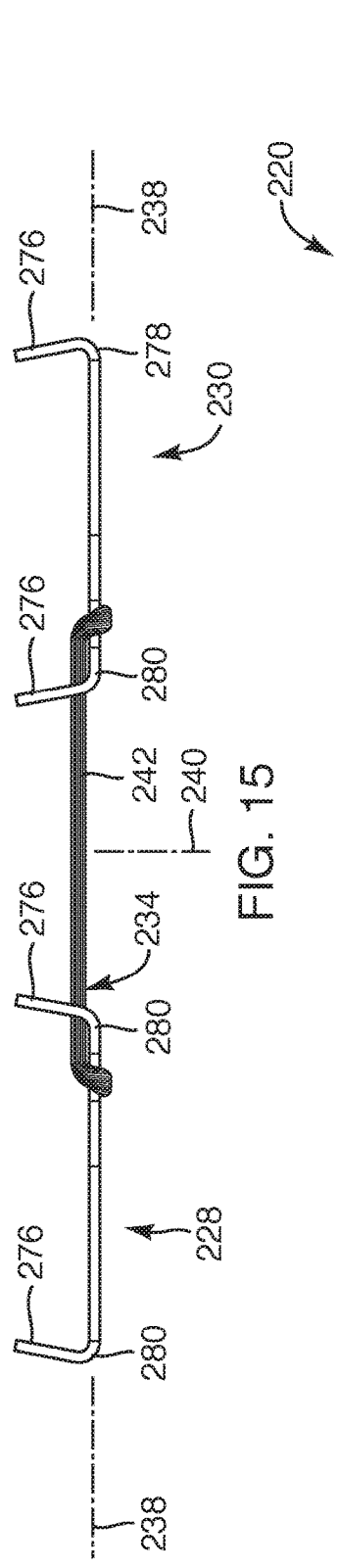
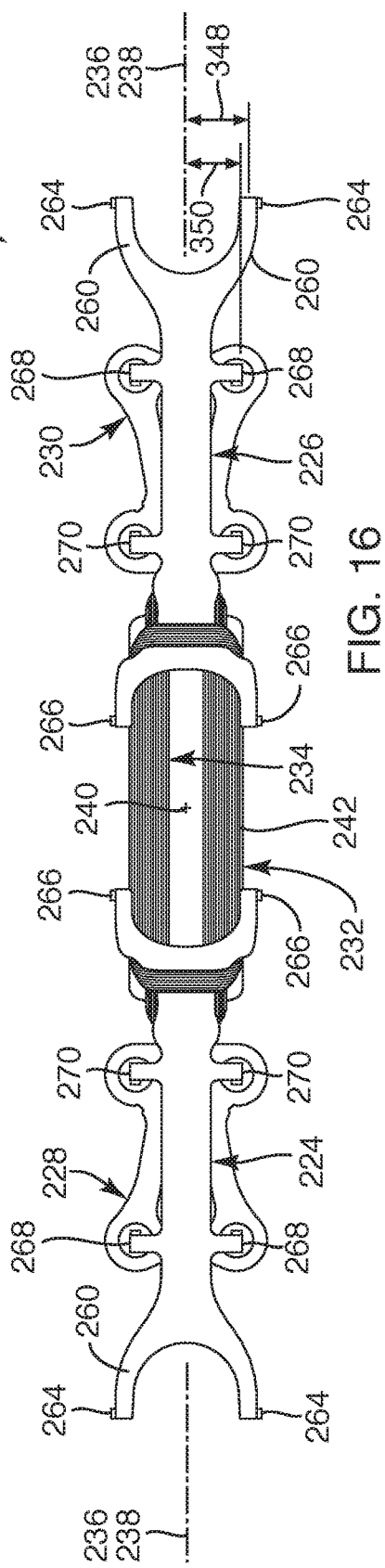
FIG. 15
FIG. 16 ial Application No. 62/581,031, filed Nov. 2, 2017, U.S.
DEVICES, SYSTEMS, AND METHODS FOR REPAIRING SOFT TISSUE AND ATTACHING SOFT TISSUE TO BONE

CROSS-REFERENCE TO RELATED APPLICATIONS

The present application claims the benefit of U.S. Provisional Application No. 62/581,031, filed Nov. 2, 2017, U.S. Provisional Application No. 62/464,300, filed Feb. 27, 2017, and U.S. Provisional Application No. 62/445,596, filed Jan. 12, 2017, the disclosures of each are hereby incorporated by reference herein in their entirety. The present application also claims the benefit, and is a continuation-in-part of, U.S. patent application Ser. No. 15/719,346, filed Sep. 28, 2017, which claims the benefit of U.S. Provisional Application No. 62/401,042, filed Sep. 28, 2016, the disclosures of which are hereby incorporated by reference herein in their entirety. Further, U.S. patent application Ser. No. 15/719,346 also claims the benefit, and is a continuation-in-part of, U.S. patent application Ser. No. 14/885,959, filed Oct. 16, 2015, now U.S. Pat. No. 10,219,804, which claims the benefit of U.S. Provisional Application No. 62/215,739, filed Sep. 9, 2015, U.S. Provisional Application No. 62/129,742, filed Mar. 6, 2015, U.S. Provisional Application No. 62/094,032, filed Dec. 18, 2014, and U.S. Provisional Application No. 62/064,533, filed Oct. 16, 2014, the disclosures of each are hereby incorporated by reference herein in their entirety. Further, U.S. patent application Ser. No. 14/885,959 also claims the benefit, and is a continuation-in-part of, U.S. patent application Ser. No. 14/645,924, filed Mar. 12, 2015, now U.S. Pat. No. 9,629,632, which claims the benefit of U.S. Provisional Patent Application No. 62/053,056, filed Sep. 19, 2014, U.S. Provisional Patent Application No. 62/040,451, filed Aug. 22, 2014, U.S. Provisional Patent Application No. 62/007,783, filed Jun. 4, 2014, and U.S. Provisional Patent Application No. 61/952,114, filed Mar. 12, 2014, the disclosures of each are hereby incorporated by reference herein in their entirety. Further, the above-listed U.S. patent application Ser. No. 14/645,924 claims the benefit, and is a continuation-in-part of, U.S. patent application Ser. No. 13/953,709, filed Jul. 29, 2013, now U.S. Pat. No. 9,427,309, which claims the benefit of U.S. Provisional Patent Application No. 61/804,570, filed Mar. 22, 2013, and U.S. Provisional Patent Application No. 61/677,239, filed Jul. 30, 2012, the disclosures of each are hereby incorporated by reference herein in their entirety.

TECHNICAL FIELD

The present invention relates generally to soft tissue repair sites. More particularly, the present invention relates to devices, systems, and methods for repairing soft tissue and attaching soft tissue to bone.

BACKGROUND

Lacerated flexor tendon repair, as an example, is a procedure performed tens-of-thousands of times a year in the United States alone. For all types of tendons in the human anatomy, early post-operative mobilization is beneficial to restoring maximal tendon function following injury and repair. Adhesion formation is a common complication following tendon repair, but can be reduced through motion rehabilitation programs as soon as possible following a surgery. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

Typical procedures for lacerated tendon repair use one or more sutures to mend the two ends of a tendon together using complex suture patterns. While this can provide a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion. Further, complex suture patterns are also used for fixating soft tissue, such as tendon and ligaments, to bone, resulting in similar negative effects to the patient and often result in subsequent procedures depending on the activity level of the patient. Furthermore, such complex suturing procedures are time consuming and typically require specialized surgeons to perform such procedures.

BRIEF SUMMARY OF THE INVENTION

Embodiments of the present invention are directed to various devices, systems and methods for repairing soft tissue at a soft tissue repair site. For example, in one embodiment, a repair device system for coupling to soft tissue is provided. The repair device system including a delivery device, an implant delivery member, and a repair device. The delivery device including a handle and a push rod defining a longitudinal axis such that the push rod is configured to linearly actuate along the longitudinal axis. The implant delivery member is configured to be removably coupled to the delivery device. The implant delivery member including a cartridge and an anvil, the cartridge linearly moveable relative to the anvil. The repair device is configured to be held within the cartridge. The repair device including an anchor with a base having at least four legs extending from the base. Upon actuating the push rod with the delivery device, the push rod is configured to move the anchor from the cartridge to move the at least four legs against the anvil to move the at least four legs from a linear position to a formed position.

In another embodiment, the repair device includes a capture member configured to be coupled to the anchor, the repair device configured to couple to soft tissue with the anchor and the capture member on opposing sides of the soft tissue. In another embodiment, the repair device includes a capture member, the capture member configured to be coupled to the anchor with the at least four legs in the formed position such that the at least four legs are formed around structure of the capture member.

In another embodiment, the base of the anchor includes an elongated structure defining a base axis and the anvil being elongated to define an anvil axis, the base axis extending substantially parallel relative to the anvil axis. In still another embodiment, the anvil is elongated to define an anvil axis, the anvil axis extending substantially perpendicular relative to the longitudinal axis of the push rod. In another embodiment, the formed position of the legs includes a curled position of the legs.

In another embodiment, upon the implant delivery member being coupled to the delivery device, the push rod is configured to couple to the cartridge. In still another embodiment, the, the delivery device includes a worm drive configured to be rotated by a thumb wheel, the worm drive configured to couple to a base portion of the implant delivery member. In still another embodiment, upon the implant delivery member being coupled to the delivery device, the at least four legs of the anchor held in the cartridge extend substantially parallel with the longitudinal axis of the push rod.

In accordance with another embodiment of the present invention, a repair device system configured to couple to soft tissue is provided. The repair device system including an anvil and at least one anchor. The anvil including an upper surface defining anvil buckets therein. The at least one anchor is operatively coupled to the anvil. The at least one anchor having a base with at least four legs extending from the base, the at least four legs configured to be compressed against the anvil buckets to move the at least four legs to a formed position.

In another embodiment, the at least one anchor includes a first anchor and a second anchor, the first anchor coupled to the second anchor with a flexible member. In a further embodiment, the flexible member includes one or more filaments.

In another embodiment, the repair device system further includes at least one capture member, the at least one capture member configured to be positioned over the upper surface of the anvil, the at least one capture member configured to be coupled to the at least one anchor with the at least four legs in the formed position such that the at least four legs are formed around structure of the at least one capture member. In another embodiment, the repair device system further includes at least one capture member configured to be positioned on the upper surface of the anvil so that some of the at least four legs couple to the at least one capture member, upon the at least four legs being compressed against the anvil buckets. In another embodiment, the repair device system further includes a bone anchor configured to be coupled to the at least one anchor with a flexible member.

In another embodiment, at least one of the anvil buckets is sized and configured to correspond with two legs of the at least four legs. In another embodiment, the upper surface of the anvil includes a first surface and a second surface each with the anvil buckets defined therein, the first surface being elevated higher than the second surface. In another embodiment, the anvil buckets defined in the upper surface of the anvil define at least two depths in the upper surface.

In accordance with another embodiment of the present invention, a repair device configured to couple to soft tissue is provided. The repair device includes a capture portion and an anchor portion. The capture portion is configured to extend with radial portions. The anchor portion includes a base with multiple legs extending therefrom, the multiple legs configured to move from a linear position to a formed position such that, in the formed position, the multiple legs couple to structure of the capture portion.

In another embodiment, the repair device further includes a flexible member coupled to at least one of the capture portion and the anchor portion, the flexible member configured to be coupled to a bone anchor. In another embodiment, the anchor portion includes a first anchor and a second anchor with a flexible member coupled therebetween.

In another embodiment, the capture portion extends with multiple apertures therein. In another embodiment, the capture portion extends with a substantially flat structure. In still another embodiment, the capture portion and the anchor portion extends with elongated structures. In another embodiment, the multiple legs of the anchor portion are sized and configured to couple to the radial portions of the capture portion.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 12 is a perspective view of another embodiment of a repair device, depicting first and second anchors with legs aligned for engagement relative to the respective first and second capture members, according to the present invention;

FIG. 13 is a top view of an anvil of a delivery device, depicting anvil buckets defined in the anvil sized for the repair device of FIG. 12, according to another embodiment of the present invention;

FIG. 15 is a side view of the repair device of FIG. 12, depicting a side profile of the first and second anchors in a disengaged position relative to the respective first and second capture members, according to another embodiment of the present invention;

FIG. 16 is a top view of the repair device of FIG. 12, depicting a top profile of the first and second anchors relative to the respective first and second capture members, according to another embodiment of the present invention;

DETAILED DESCRIPTION OF THE INVENTION

Various embodiments are disclosed herein of a soft tissue repair device that may be employed to fixate severed or ruptured soft tissue together or for coupling soft tissue to bone. For example, the various embodiments of a repair device may provide structure that maintains two ends or end portions of a lacerated or ruptured tendon in an abutting relationship, without gapping, to facilitate the appropriate healing required for fusing ends or end portions of soft tissue. In some embodiments, the structural characteristics of the repair device may allow the tendon adjacent the tendon ends and along the length of the repair device to provide controlled elongation of the tendon.

Figure 1:
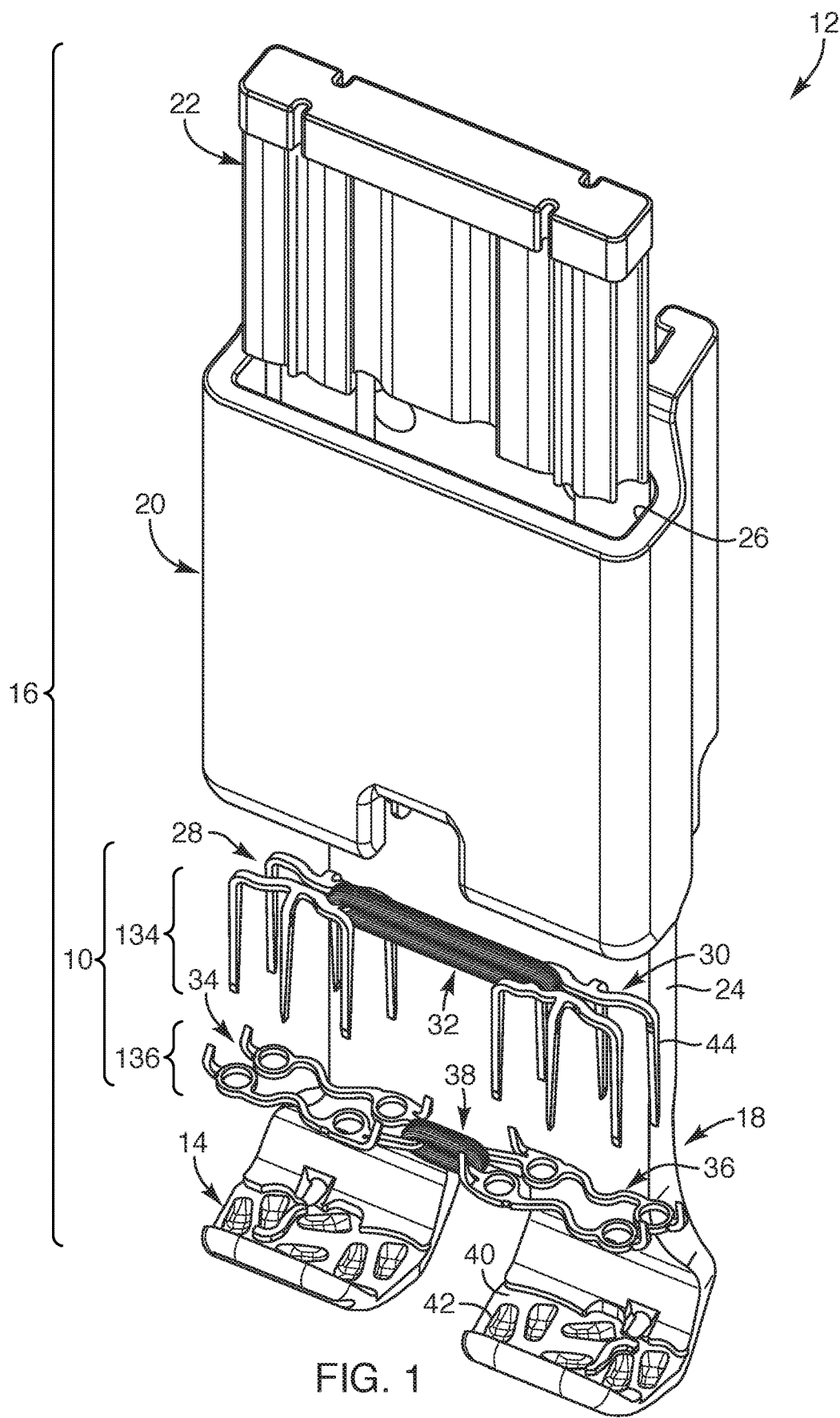
FIG. 1 is an exploded perspective view of various components of a distal portion of a delivery device configured to deliver a repair device, according to an embodiment of the present invention.
Figure 2:
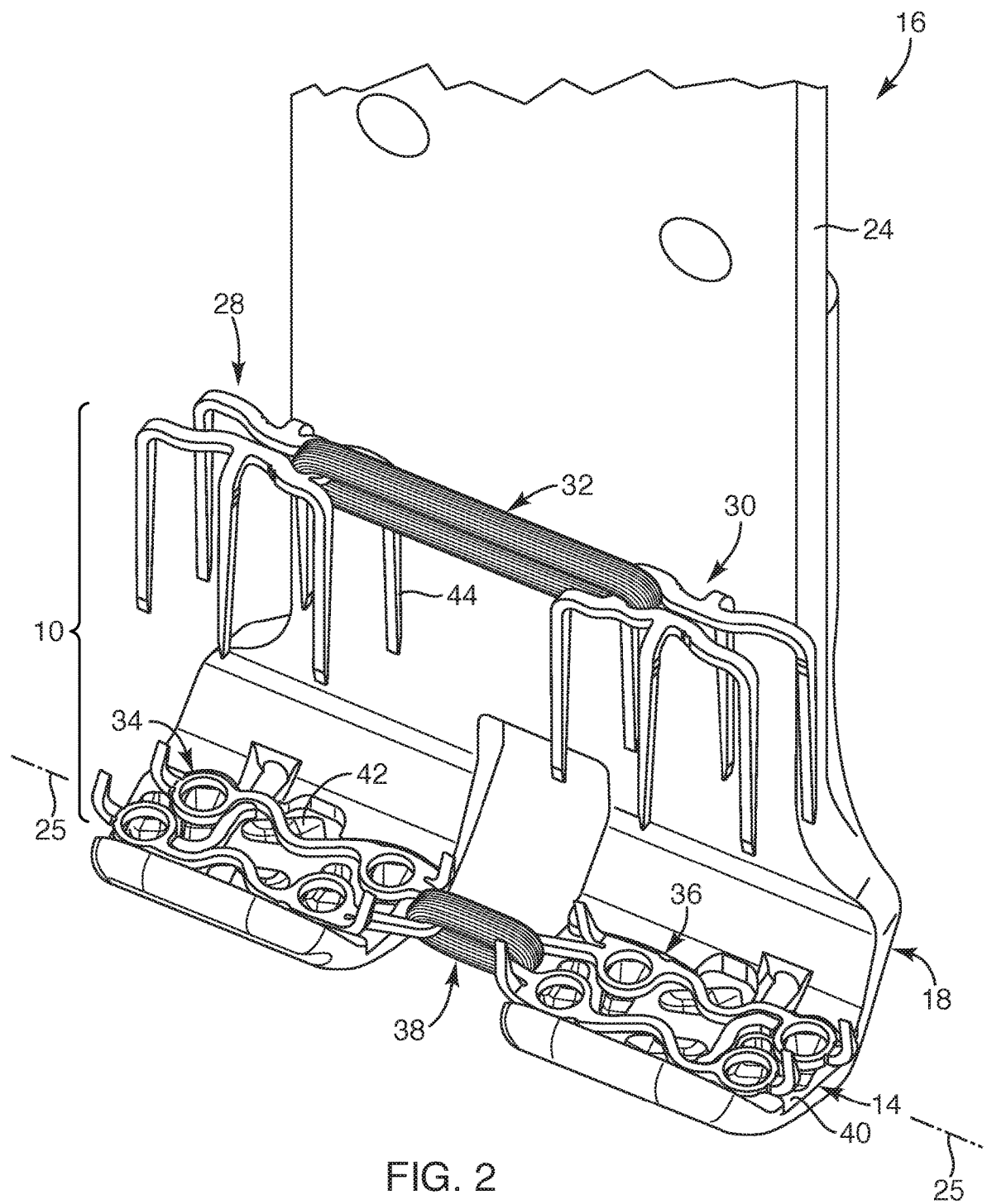
FIG. 2 is a perspective view of the repair device and a cradle portion, depicting first and second anchors in a pre-deployed state as positioned within the cartridge (not shown) and positioned above first and second capture members in the cradle portion, according to another embodiment of the present invention.

With reference to FIGS. 1 and 2, in one embodiment, a repair device 10 may be deployed into soft tissue 11, such as tendon or ligament, and delivered with a delivery device 12 (FIG. 3) with an anvil 14 at an end portion 16 of the delivery device 12. The end portion 16 of the delivery device 12 may include a cradle 18, a cartridge 20 and a pusher member 22, each of which may be sized and configured to cooperate with the repair device 10. The cartridge 20 may be linearly slidable and coupled to a rail portion or tract of an elongated extension 24 of the cradle 18 with a c-arm or channel extending along an underside of the cartridge 20. The cartridge 20 may be hollow or define a hollow portion so as to define an opening 26 extending through opposite sides of the cartridge 20 with the pusher member 22 positionable within a proximal side of the opening 26 of the cartridge 20 and a portion of the repair device 10 positionable within a distal side of the opening 26 of the cartridge 20.

Figure 7:
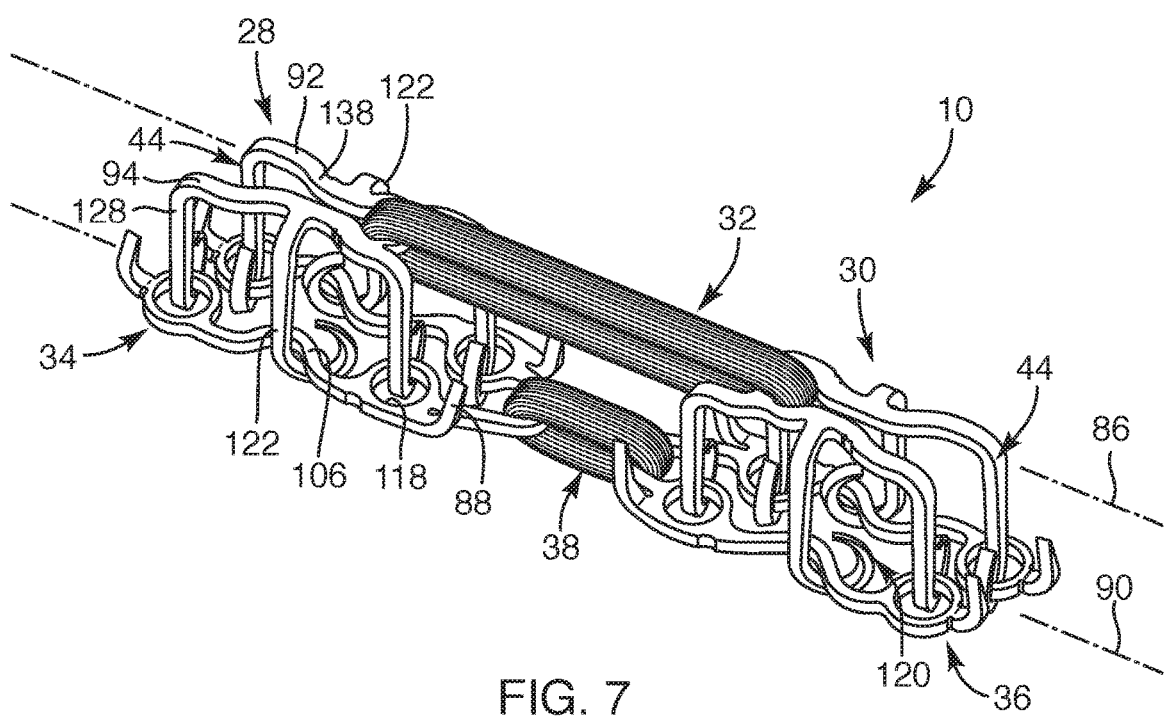
FIG. 7 is a perspective view of the repair device, depicting the repair device in a deployed state, according to another embodiment of the present invention.

The repair device 10 may include a first anchor 28 coupled to a second anchor 30 with a first flexible member 32 therebetween. The before-mentioned portion of the repair device 10 positioned within the distal side of the cartridge 20 may be such first and second anchors 28, 30 with the first flexible member 32 therebetween. Further, in another embodiment, the repair device 10 may also include a first capture member 34 and a second capture member 36 with a second flexible member 38 coupling the first capture member 34 to the second capture member 36. Such first and second capture members 34, 36 may be positioned over an upper surface 40 of the anvil 14. Such anvil 14 may include anvil buckets 42 defined in the upper surface such that the anvil buckets 42 may be sized, oriented, and configured to manipulate legs 44 of the first and second anchors 28, 30. Further, the anvil 14 may define elongated structure to define a longitudinal anvil axis 25 extending along the elongated structure. With this arrangement, the first and second anchors 28, 30 can be temporarily housed within the cartridge 20 and effectively deployed from the cartridge 20 with the pusher member 22 so that the legs 44 of the first and second anchors 28, 30 compress into the anvil buckets 42 to bend or move the legs 42 of the first and second anchors 28, 30 to a formed position, such as a curled position, to be coupled to the first and second capture members 34, 36, as depicted in FIG. 7, discussed in further detail herein.

Now with reference to FIGS. 3, 4 and 5A, the delivery device 12 sized and configured to deploy the repair device 10 (FIG. 2) will now be described. The delivery device 12 may include a trigger gun 46 with a trigger 48. The trigger gun 46 may be manually actuatable in a physician's hand by manually gripping or actuating the trigger 48, as shown with arrow 50. The delivery device 12 may also include a barrel housing 52 defining an axis 54. The barrel housing 52 may house a worm drive 56 and a push rod 58 co-axial with the worm drive 56 and extending longitudinally through the worm drive 56. Such push rod 58 may be configured to cooperate with the trigger 48 so as to distally actuate upon actuating the trigger 48. The barrel housing 52 may also include one or more openings 60 or opposing openings defined therein such that a thumb wheel 62 may be positioned and accessible for manually rotating therein. Further, the delivery device 12 includes a replaceable and removable implant delivery member 64 such that the implant delivery member 64 may be removable relative to the barrel housing 52.

Figure 3:
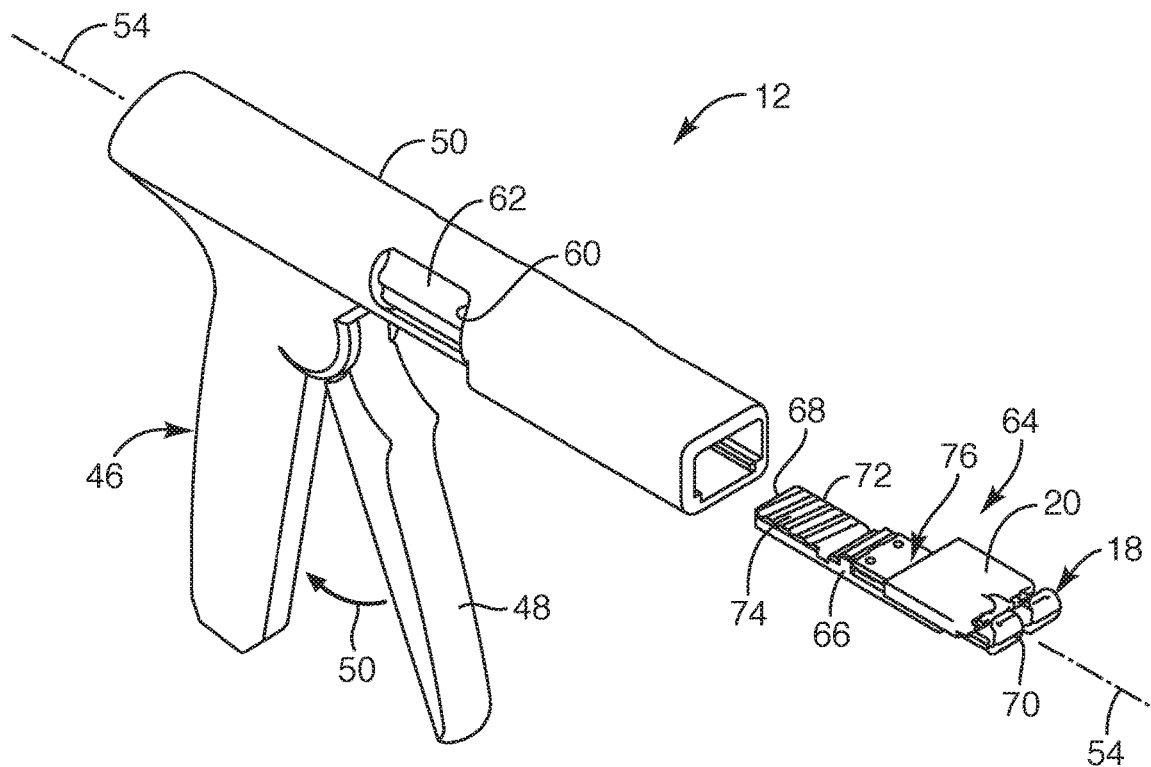
FIG. 3 is a perspective view of the delivery device, depicting the delivery device with an implant delivery member in a non-engaged position, according to another embodiment of the present invention.
Figure 4:
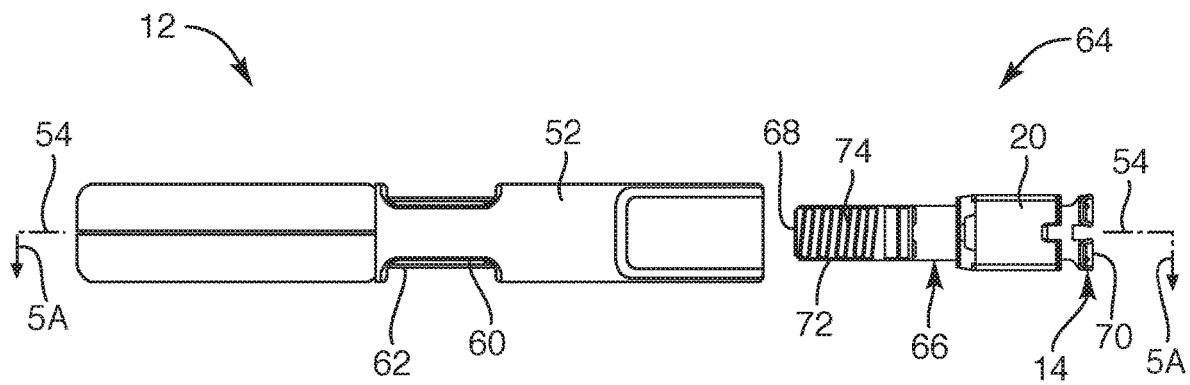
FIG. 4 is a top view of the delivery device of FIG. 3, according to another embodiment of the present invention.

With respect to FIGS. 1, 3 and 4, the implant delivery member 64 may include a base portion 66, the cartridge 20 and the cradle 18, the implant delivery member 64 extending between a proximal end 68 and a distal end 70. The base portion 66 may be coupled to the elongated extension 24 of the cradle 18 so as to extend proximally from the cradle 18 to define a tongue 72. Such tongue 72 may include threads 74 along an upper side 76 of the tongue 72 of the implant delivery member 64. The base portion 66 may also include a track or other structural characteristics that facilitate the cartridge 20 to be linearly moveable or slidable between the anvil 14 and the tongue 72 along the upper side 76 of the implant delivery member 64. The cradle 18 may include the anvil 14 with the upper surface 40 with the anvil buckets 42 defined therein.

Figure 5A:
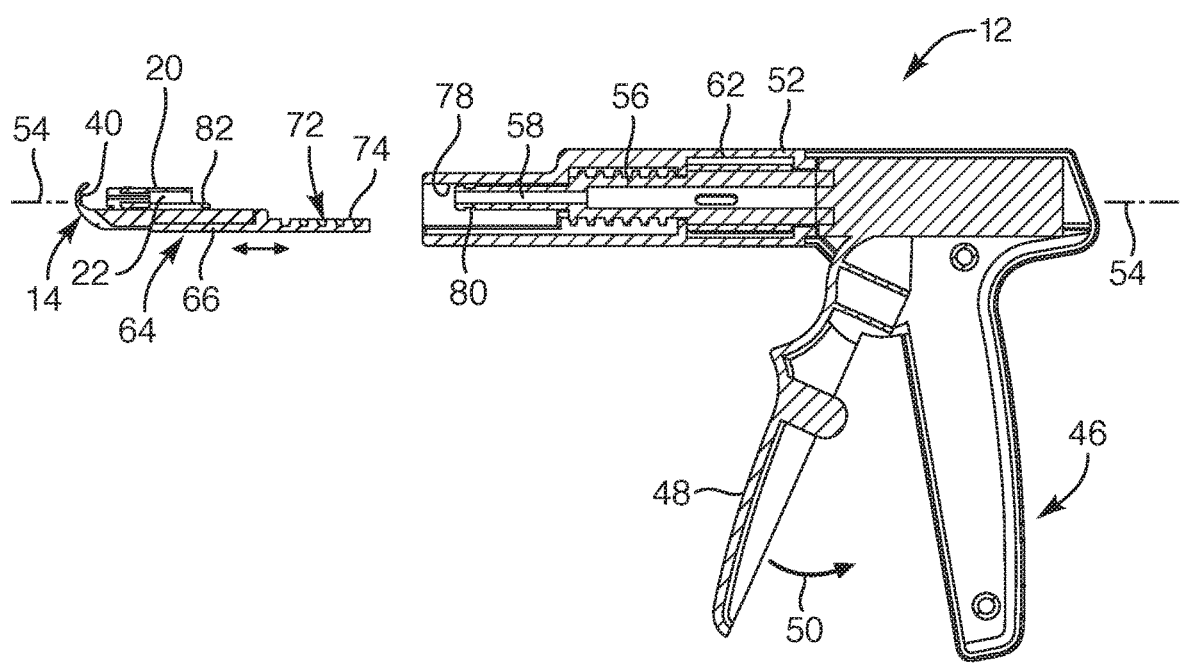
FIG. 5A is a cross-sectional view of the delivery device taken along section line 5A of FIG. 4, depicting the implant delivery member disengaged relative to a pusher member portion of the delivery device, according to another embodiment of the present invention.
Figure 5B:
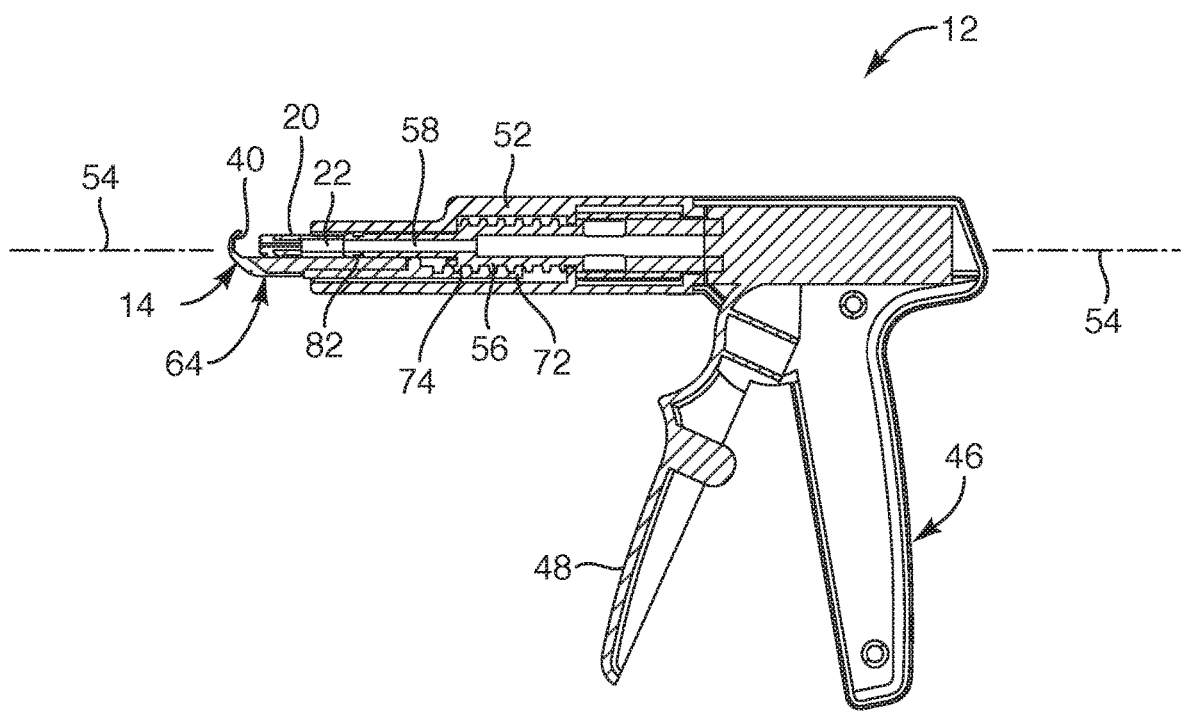
FIG. 5B is a cross-sectional view of the delivery device, depicting the implant delivery member engaged with the pusher member portion of the delivery device, according to another embodiment of the present invention.

With reference to FIGS. 3, 5A and 5B, the thumb wheel 62 of the delivery device 12 may be manually rotatable to cooperate with the worm drive 56. As such, the physician may position the tongue 72 within an end opening 78 or within a bore of the barrel housing 52 and, for example, position the tongue 72 within a space below the push rod 58. Once positioned, the physician may rotate the thumb wheel 62 so that the worm drive 56 may engage the threads 74 of the tongue 72 and linearly move and pull the base portion 66 within the barrel housing 52. Upon engaging the tongue 72, the physician may continue to rotate the thumb wheel 62 so that the base portion 66 continues proximally so that the push rod 58 moves and slides the cartridge 20 distally until the cartridge 20 abuts and stops against the anvil 14 of the cradle 18. The push rod 58 may include a recess 80 at a distal end portion of the push rod 58. Upon the cartridge 20 being moved to a distal stop against the anvil 14 or cradle, further movement of the thumb wheel 62 may move the push rod 58 over a lip 82 adjacent a proximal side of the cartridge 20 so that the recess 80 in the push rod 58 engages and may be captured by the lip 82. The physician may hear, for example, a click as an assurance that the cartridge 20 is engaged with the push rod 58. At this juncture, the push rod 58 may be engaged with the cartridge 20 such that reverse movement of the thumb wheel 62 may move the push rod 58 and the cartridge 20 proximally. The physician may then move the cartridge 20 proximally a desired distance to then position soft tissue (not shown) in the cradle 18. Once the soft tissue is positioned along the upper surface 40 of the cradle 18, the trigger 48 of the delivery device 12 may be actuated to move the push rod 58 distally, extending along the axis 54, to push against the pusher member 22 to then push the repair device 10 from the cartridge 20 and into the soft tissue. As previously set forth, as the legs 44 of the first and second anchors 28, 30 compress against the anvil buckets 42, the legs 44 move to a formed or curled position to wrap around portions of the first and second capture members 34, 36 (see FIGS. 2 and 7). At this juncture, the physician may then rotate the thumb wheel 62 to move the base portion 66 and cradle 18 distally so that the cartridge 20 is backed-off from the cradle 18 and so that the user may then readily remove the soft tissue with the deployed repair device 10 therein and from the cradle 18.

If it is desired to implant a second repair device in the soft tissue, the user may then continue to rotate the thumb wheel 62 to continue to move the implant delivery member 64 distally until the worm drive 56 is disengaged from the threads 74 of the tongue 72 of the implant delivery member 64. At this stage, the physician may take a second one of the implant delivery member 64 and position it within the barrel housing 52 for engaging with the delivery device 12 as described above to then position a second repair device in the soft tissue, if desired. In this manner, the implant delivery member 64 is removable and replaceable relative to the delivery device 12 so that the delivery device 12 may be repeatably employed with multiple implant delivery members 64.

The components of the delivery device 12 may be formed and made with medical grade materials, such as stainless steel, titanium, Nitinol, and/or alloys thereof or any other suitable metallic material or polymeric materials, such as liquid crystal polymers or acrylonitrile butadiene styrene ("ABS") or any other suitable polymeric materials known to one of ordinary skill in the art. Such delivery device 12 components may be formed by employing molding and/or machining techniques, or any other suitable techniques and processes known to one of ordinary skill in the art.

Figure 6:
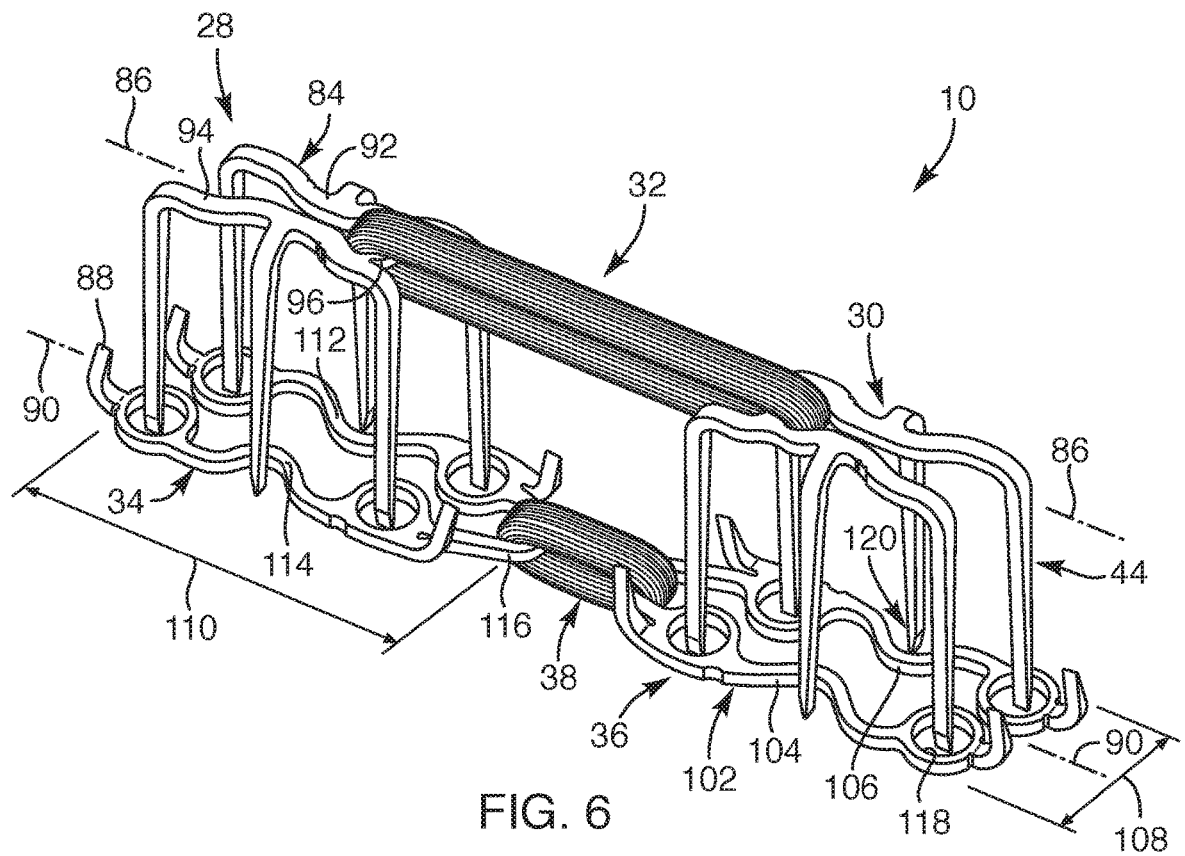
FIG. 6 is a perspective view of the repair device, depicting the first and second anchors with legs aligned for engagement relative to the respective first and second capture members, according to another embodiment of the present invention.

Now with reference to FIGS. 6-8, the repair device 10 previously described relative to FIGS. 1 and 2 will now be described in further detail. Various components of the repair device 10 may be initially cut and formed from sheet material. For example, the first and second anchors 28, 30 may be cut from sheet material such that each of the first and second anchors 28, 30 may be a seamless unitary and monolithically formed structure. Once cut from the sheet material, the legs 44 of the first and second anchors 28, 30 may be bent and oriented in a generally common predetermined direction, as depicted in FIG. 6, from a single side of the first and second anchors 28, 30. Similarly, the first and second capture members 34, 36 may each be formed from sheet material such that the first and second capture members 34, 36 may be a seamless unitary or monolithically formed structure, which may include portions bent and oriented as depicted in FIG. 6. The first and second anchors 28, 30 and the first and second capture members 34, 36 may be formed from, for example, a medical grade sheet material, such as stainless steel, titanium, Nitinol, and/or alloys thereof or any other suitable medical grade material, and be cut from the sheet material by laser cutting or any other suitable cutting technique known by one of ordinary skill in the art. In another embodiment, the sheet material may be a bioresorbable material such as zinc, polylactic-co-glycolic acid ("PLGA") or any other suitable bioresorbable material described herein or known by one of ordinary skill in the art.

With respect to FIG. 6, the repair device 10 is depicted with the legs 44 of the first and second anchors 28, 30 positioned and oriented relative to the first and second capture members 34, 36 just before the legs 44 are being compressed into the anvil buckets 42 of the anvil 14 (see FIG. 2). Further, the first and second anchors 28, 30 may each include a base that may define elongated structure with legs 44 extending therefrom. The base 84 of the first and second anchors 28, 30 may be longitudinally aligned and oriented relative to each other and coupled together with the first flexible member 32 so as to define an anchor axis 86. Similarly, the first and second capture members 34, 36 may define elongated structure with tines 88 extending therefrom such that the first and second capture members 34, 36 may be longitudinally aligned and oriented with the second flexible member 38 extending therebetween so as to define a capture member axis 90. In this manner, the first and second anchors 28, 30 may be longitudinally aligned and oriented relative to the first and second capture members 34, 36 so that the anchor axis 86 extends substantially parallel relative to the capture member axis 90. Further, each of the anchor axis 86 and the capture member axis 90 may be extend substantially parallel with the anvil axis 25 (FIG. 2). Even further, the anchor axis 86 and the capture member axis 90 may extend substantially perpendicular relative to the axis 54 of the delivery device 12 (FIG. 3).

As set forth, the first and second anchors 28, 30 may each include a base 84 with legs 44 extending from the base 84. The base 84 of each of the first and second anchors 28, 30 may extend generally within a plane. Subsequent to the first and second anchors 28, 30 being cut from sheet material, the legs 44 may be bent at their respective base to a bent position as depicted. In one embodiment, the base 84 of each of the first and second anchors 28, 30 may include a first elongate portion 92 and a second elongate portion 94. The first and second elongate portions 92, 94 may be interconnected by a laterally extending portion 96 therebetween. Such laterally extending portion 96 may be employed for coupling the first flexible member 32 thereto for each of the first and second anchors 28, 30.

As set forth, each of the first and second anchors 28, 30 include multiple legs 44 extending from a single side of the base 84. In one embodiment, each of the first and second anchors 28, 30 may include six legs 44 or more. In another embodiment, each of the first and second anchors 28, 30 may include at least five legs 44. In still another embodiment, each of the first and second anchors 28, 30 may include at least four legs 44. In yet another embodiment, each of the first and second anchors 28, 30 may include at least three legs 44. In some embodiments, the number of legs 44 for a given anchor may correspond with structural portions (i.e., apertures, struts, curved portions, etc.) of the first and second capture members 34, 36, the structural portions sized and configured to be captured or coupled to the legs 44, discussed in further detail herein. Each of the legs 44 may extend generally or substantially perpendicular relative to a plane defined by the base 84 of each of the first and second anchors 28, 30.

As set forth, the first and second anchors 28, 30 may be coupled together with the first flexible member 32. The first flexible member 32 may include one or more filaments. Such one or more filaments of the first flexible member 32 may be wrapped over the laterally extending portion 96 of each base 84 or a neck portion or any other suitable portion of the first and second anchors 28, 30. The one or more filaments of the first flexible member 32 may take multiple wrappings or windings to ensure the first and second anchors 28, 30 are appropriately coupled together so as to substantially resist elongation. The first flexible member 32 may be formed from any suitable medical grade filament, such as a biocompatible polymeric filament or the like, for example, ultra-high molecular weight polyethylene. In another embodiment, the first flexible member 32 may be a single flexible member or include multiple flexible members extending between the first and second anchors 28, 30.

The first and second capture members 34, 36 may each include a main body 102 having a periphery 104 or peripheral sides extending to define opposite face surfaces or sides of the main body 102. The opposing face surfaces of the main body 102 of the first and second capture members 34, 36 may be generally planar so as to exhibit a substantially flat profile. The first and second capture members 34, 36 may be referenced as a plate member, a substrate or backing member of the repair device 10. The periphery 104 of the main body 102 may define inner and outer peripheral portions that may extend to exhibit a generally u-shaped configuration such that portions of the u-shaped configuration may exhibit radial portions or curved portions 106. The first and second capture members 34, 36 may each define a width 108 and a length 110. Further, the first and second capture members 34, 36 may include the tines 88 extending transverse relative to the planar main body 102 and sized and configured to pierce and extend into soft tissue.

In one embodiment, the tines 88 of the first and second capture members 34, 36 may be canted toward the repair site. In another embodiment, the tines 88 may be canted away from the repair site. In still another embodiment, the tines 88 may extend substantially perpendicular relative to the main body 102 of the first and second capture members 34, 36. But for the tines 88, the first and second capture members 34, 36 may extend in a plane or be substantially flat since the capture members may be laser cut from sheet material and, as such, portions of the cut sheet material may be flat and plate like and may exhibit a square or rectangular cross-section. In another embodiment, the tines 88 may include a barb or the like extending therefrom.

In one embodiment, each of the first and second capture members 34, 36 may include first and second elongated portions 112, 114 extending from an inner portion 116. At each inner portion 116 of the first and second capture members 34, 36, the second flexible member 38 may be employed to couple the first capture member 34 to the second capture member 36. Further, the first and second elongated portions 112, 114 may each define one or more apertures 118 therein and/or the one or more curved portions 106. The apertures 118 and/or the curved portions 106 may be sized and configured to receive and be captured by the legs 44 of the first and second anchors 28, 30, described in further detail herein.

As previously set forth, the first and second capture members 34, 36 may be coupled together with the second flexible member 38. Similar to the first flexible member 32, the second flexible member 38 may include one or more filaments. In one embodiment, such one or more filaments of the second flexible member 38 may be wrapped over and around the inner portion 116 of each main body 102 of the first and second capture members 34, 36. The one or more filaments of the second flexible member 38 may take multiple wrappings or windings to ensure the first and second capture members 34, 36 are appropriately coupled together. The second flexible member 38 may be formed from any suitable medical grade filament, such as a biocompatible polymeric filament or the like, for example, ultra-high molecular weight polyethylene. In another embodiment, the second flexible member 38 may be a single flexible member or include multiple flexible members extending between the first and second capture members 34, 36.

Figure 8:
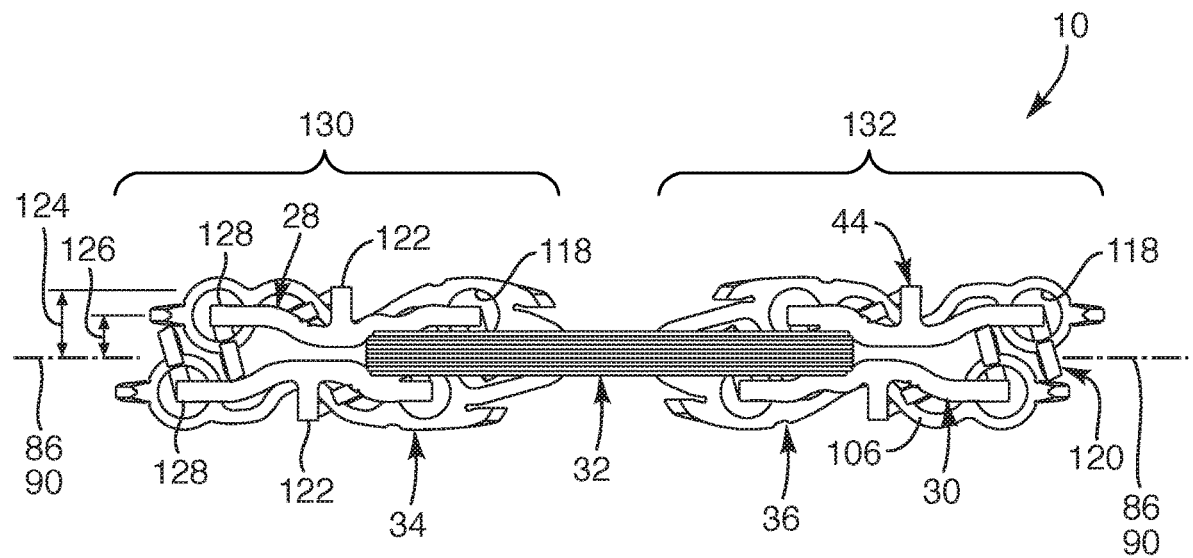
FIG. 8 is a top view of the repair device of FIG. 7, according to another embodiment of the present invention.
Figure 9:
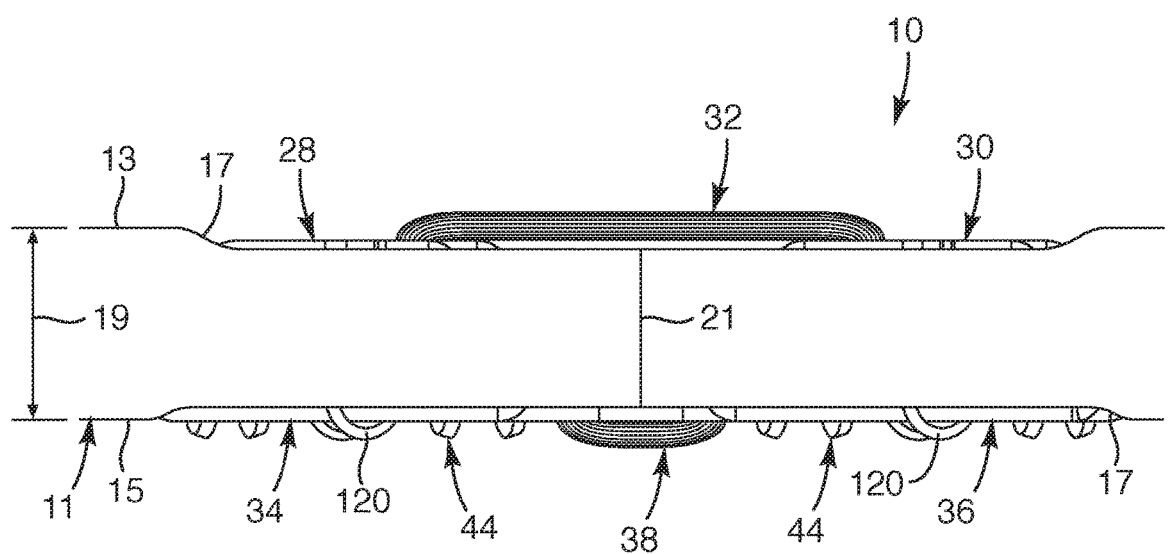
FIG. 9 is a side view of the repair device, depicting the repair device deployed within soft tissue at a soft tissue repair site, according to another embodiment of the present invention.

Now with reference to FIGS. 7-8, upon the legs 44 of the first and second anchors being compressed into the anvil buckets 42 of the anvil 14 (see FIG. 2), as previously set forth herein, end portions 120 of legs 44 of the first and second anchors 28, 30 may be moved (forced and compressed) to a formed position. In this manner, such end portions 120 of the legs 44 of each of the first and second anchors 28, 30 may be moved from a first position (generally linear position, depicted in FIG. 6) to a second position, as depicted in FIG. 7. The second position of the legs 44 may exhibit a formed position, such as a bent, curled or wrapped position, formed via being compressed into the anvil buckets 42 of the anvil 14 (FIG. 2). In this manner, the end portions 120 of the legs 44 may be manipulated to bend or wrap around structural portions of the first and second capture members 34, 36, thereby, coupling the first and second anchors 28, 30 to the respective first and second capture members 34, 36.

As previously set forth, the first and second capture members 34, 36 may each extend to define one or more apertures 118 and/or curved portions 106 and/or any other suitable capturing structure or structural portions, such as notches or peripheral recesses. Such capturing structure, such as apertures 118, notches, or curved portions 106, of the first and second capture members 34, 36 may be sized and configured to correspond with the legs 44 of the respective first and second anchors 28, 30 to facilitate the legs 40 to wrap or curl around the structural portions of the first and second capture members 34, 36.

With respect to FIG. 8, in one embodiment, at the first side or upper side of the soft tissue, the legs 44 of the first and second anchors 28, 30 extend into the soft tissue such that adjacent positions of initial entrance into the soft tissue by the legs 44 may not be longitudinally aligned with each other. For example, middle legs 122 (see FIG. 7) may extend from the first and second anchors 28, 30 a first distance 124 from the anchor axis 86 of the first and second anchors 28, 30, and other ones of the legs 44 on opposite ends of the first and second anchors 28, 30 may extend relative to the anchor axis 86 of the first and second anchors 28, 30 a second distance 126, the first distance 124 being larger than the second distance 126. In another embodiment, the first distance 124 may be smaller than the second distance 126. Similarly, in one embodiment, the adjacent positions of entrance into the soft tissue at the second side or bottom side of the soft tissue of the end portions 120 of the legs 44 relative to the tines 88 of the first and second capture members 34, 36 may not be longitudinally aligned. In other words, the end portions 120 of the legs 44 may be positioned at different distances than the tines 88 relative to the capture member axis 90 of the first and second capture members 34, 36. Further, in still another embodiment, the lateral spacing between adjacent pairs of legs 44, such as outer legs 128 relative to the middle legs 122 (see FIG. 7), may be different or longitudinally offset relative to each other. Such varying spacing or offset leg pairs 44 relative to adjacent leg pairs 44 may result in the tips of, for example, the outer legs 128 and the middle legs 122 to enter the soft tissue at varying lateral positions relative to the anchor axis 86 or axis of the soft tissue (not shown) to gather varying longitudinal tissue bundles with the formed position of the legs 44, upon deploying and fixating the repair device 10 to the soft tissue. In this manner, as a force or load is placed upon the soft tissue with the repair device 10 fixated thereto, the longitudinally extending tissue fibers may be less apt to longitudinally tear along a common longitudinal line within the soft tissue and where adjacent arms 44 extend through the soft tissue. In another embodiment, the legs 44 of the first and second anchors 28, 30 extending from one lateral side of the base 84 may be substantially longitudinally aligned relative to each other and the legs 44 of the first and second anchors 28, 30 extending from the other lateral side of the base 84 may be substantially longitudinally aligned relative to each other.

Furthermore, by coupling the legs 44 of the first and second anchors 28, 30 to wrap around structural portions of the first and second capture members 34, 36, a force or load that may be placed on the soft tissue may be maximized without the repair device 10 being pulled out of the soft tissue. In other words, the soft tissue may fail before the low profile repair device 10 fails such that the repair device 10 may remain intact and coupled together.

With continued reference to FIG. 8, in another embodiment, the repair device 10 may include a first portion 130 and a second portion 132, the first portion 130 and the second portion 132 coupled with the first flexible member 32 and the second flexible member 38. The first portion 130 may include the first anchor 28 and the first capture member 34, the first anchor 28 sized to couple to the first capture member 34 via the legs 44 of the first anchor 28. The second portion 132 may include the second anchor 30 and the second capture member 36, the second anchor 30 sized to couple to the second capture member 36 via the legs 40 of the second anchor 30. In another embodiment, the first portion 130 or the second portion 132 of the repair device 10 may be employed to be fixated to soft tissue with a flexible member coupled to, for example, a bone anchor, similar to that depicted in FIGS. 11A and 11B. Such first portion 130 and/or second portion 132 may be appropriately sized relative to the soft tissue such that the repair device 10 may be employed for fixating to soft tissue.

In another embodiment, as best depicted in FIG. 1, the repair device 10 may include an anchor portion 134 and a capture portion 136. The anchor portion 134 extending longitudinally with the first and second anchors 28, 30 and the first flexible member 32 extending longitudinally therebetween to define a mid portion of the anchor portion 134. The capture portion 136 may extend longitudinally with the first and second capture members 34, 36 and the second flexible member 38 extending longitudinally therebetween to define a mid portion of the capture portion 136. In this manner, the repair device 10 may be defined with an anchor portion 134 sized and configured to be coupled to a capture portion 136 with soft tissue fixated therebetween, as depicted in FIGS. 10A and 10B.

With respect to FIGS. 7, 9, 10A, and 10B, as set forth, the repair device 10 may be coupled together and fixated to soft tissue 11. Upon the repair device 10 being clamped or fixated to the soft tissue 11, exposed portions of the repair device 10 may exhibit a low profile relative to a first side 13 and second side 15 of the soft tissue 10. Further, the repair device 10 may create a recess 17 or depressed portion (on both the first and second sides 13, 15) in the soft tissue 11 such that exposed portions of the repair device 10 provide minimal structure extending beyond a height 19 or diameter of the soft tissue 11. As depicted, the repair device 10 may be secured and maintained to the soft tissue 11 with the legs 44 and tines 88 at multiple locations in the soft tissue 11. For example, at the first side 13 of the soft tissue 11, the legs 44 of the first and second anchors 26, 30 extend into the first side 13 and through the soft tissue 11 and back into the second side 15 of the soft tissue 11. At the second side 15 of the soft tissue, tines 88 extending from the first and second capture members 34, 36 may extend into the soft tissue 11 as well as end portions 120 of the legs 44 extending into the soft tissue 11. Further, as depicted, the first flexible member 32 extends over a tissue repair site 21 and couples the first anchor 28 to the second anchor 30. Similarly, the second flexible member 38 extends over the opposite side of the tissue repair site 21 and couples the first capture member 34 to the second capture member 36. Such first and second flexible members 32, 38 may resist elongation along their respective longitudinal lengths to substantially prevent gapping at the soft tissue repair site 21. Further, depending upon the soft tissue 11 being repaired, such as a flexor tendon, such first and second flexible members 32, 38 may assist the repair device 10 to move over a radius.

Figure 10A:
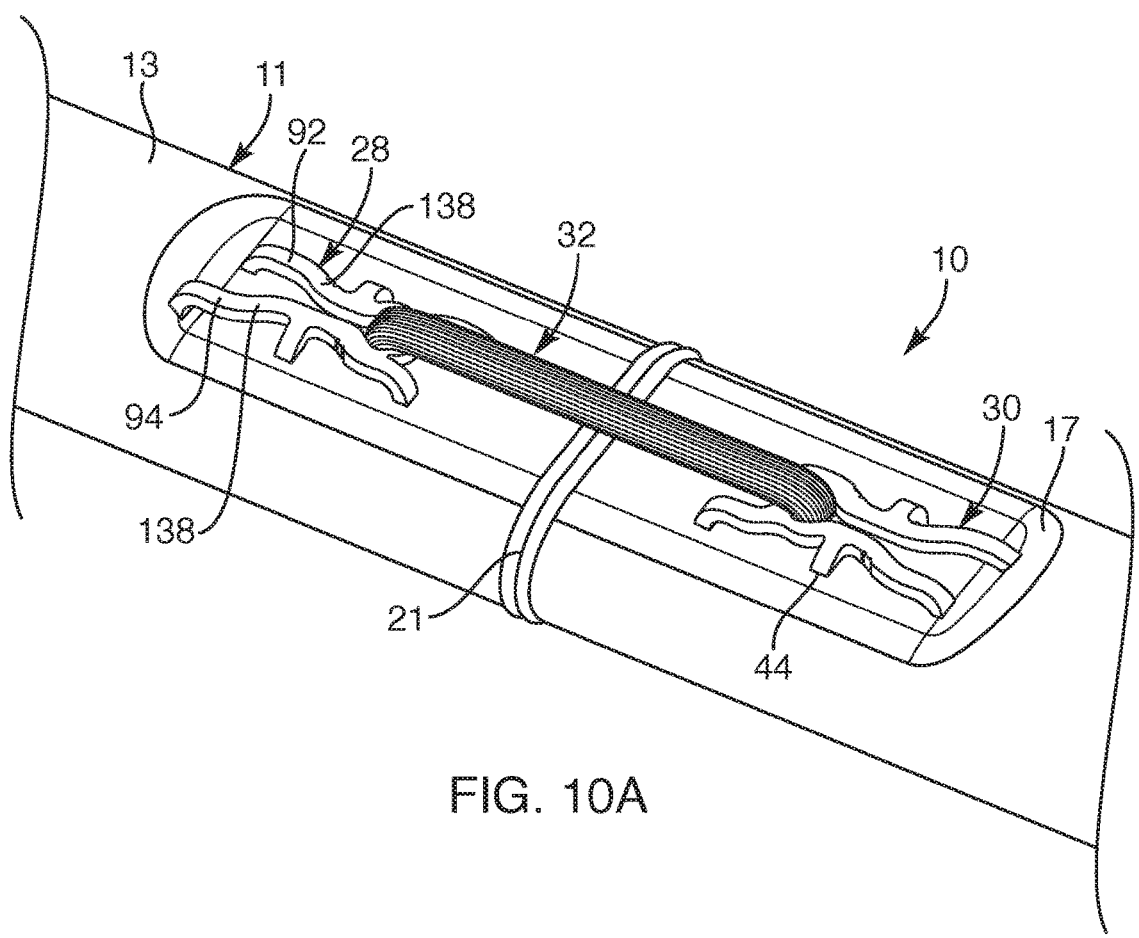
FIG. 10A is a top perspective view of the repair device deployed in the soft tissue of FIG. 9, according to another embodiment of the present invention.
Figure 10B:
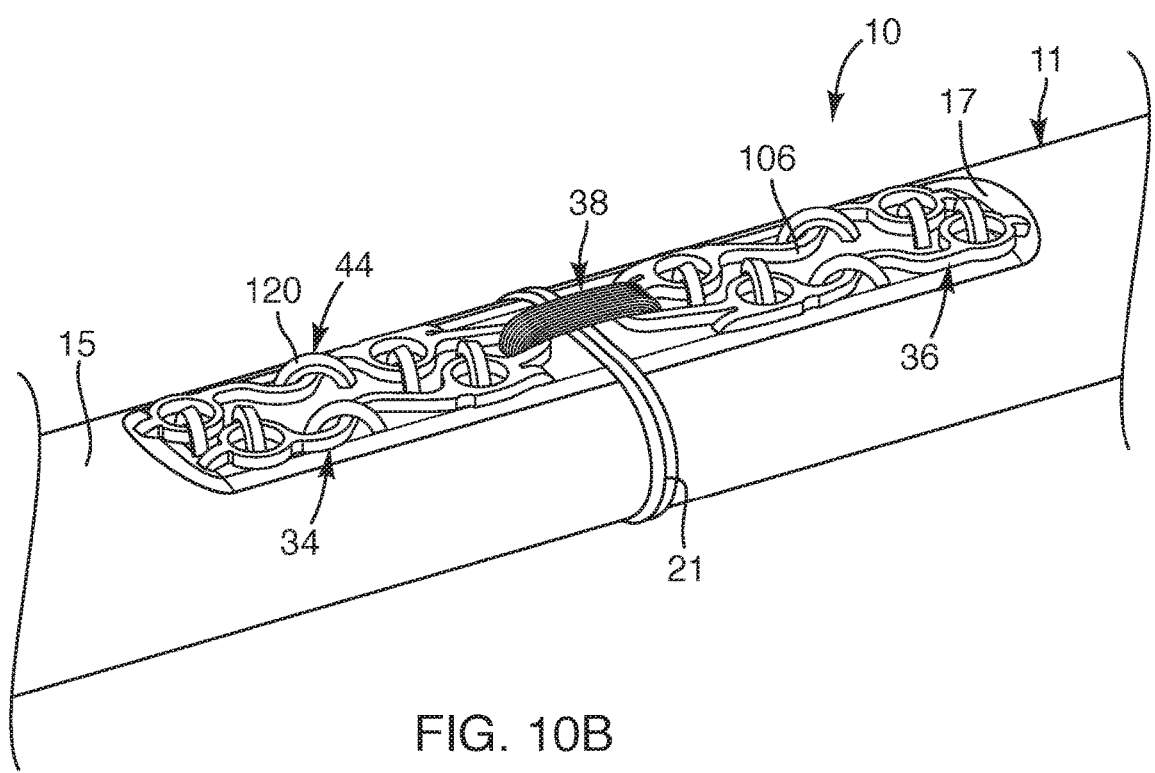
FIG. 10B is a bottom perspective view of the repair device deployed in soft tissue of FIG. 9, according to another embodiment of the present invention.

Now with reference to FIGS. 7, 10A and 10B, in another embodiment, the first and second elongate portions 92, 94 of each of the first and second anchors 28, 30 may each include a curved portion 138 along a length thereof. In one embodiment, the curved portion 138 may be sized and configured to facilitate the base 84 or the respective first and second elongate portions 92, 34 to stretch or elongate relative to the first flexible member 32 or mid portion so as to move toward a more linear configuration upon a force or load being applied to the soft tissue 11 and, thus, to the repair device 10. Similarly, the curved portions 106 of the first and second capture members 34, 36 may be sized so as to facilitate the first and second capture members 34, 36 to elongate or move to a more linear position so that the length of the first and second capture members 34, 36 elongates so as to become longer. In this manner, in one embodiment, the repair device 10 along the first and second anchors 28, 30 and the first and second capture members 34, 36 may elongate along their respective portions or lengths, upon a load being placed upon the repair device 10, while the first and second flexible members 32, 38 positioned over the soft tissue repair site 21 may resist elongation to maintain a substantially fixed position. In this manner, the soft tissue 11 may be somewhat exercised while maintaining the abutted soft tissue ends at the soft tissue repair site 21 in a substantially fixed position.

Figure 11A:
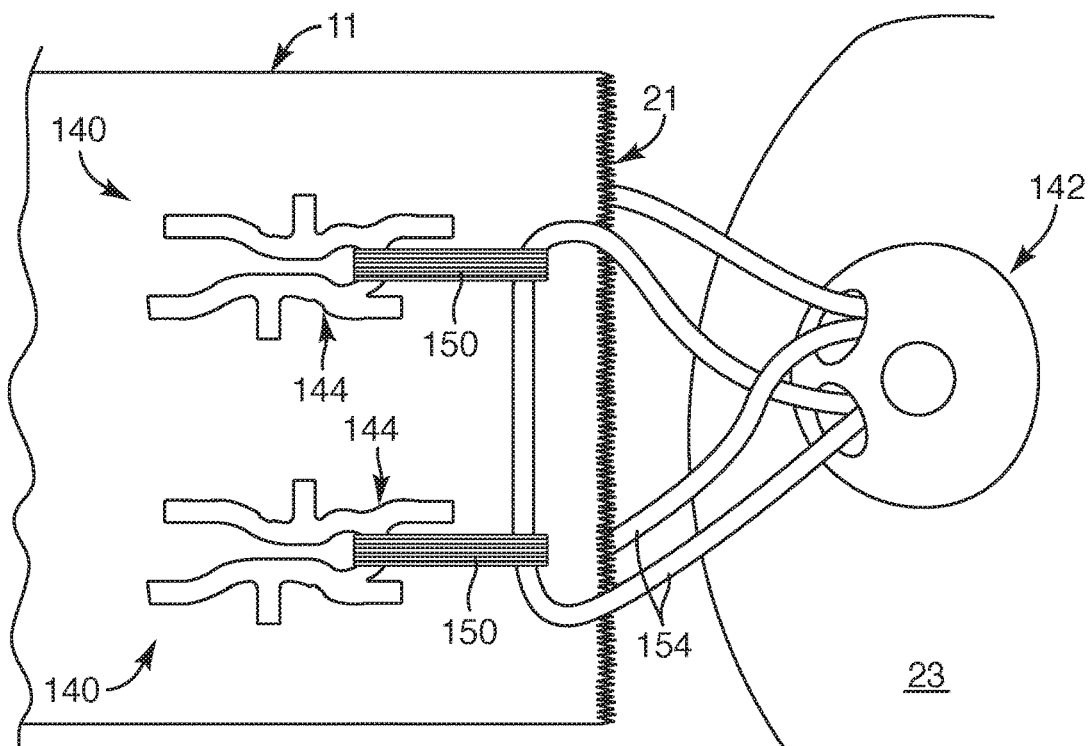
FIG. 11A is a top view of one or more repair devices, depicting first anchors of the one or more repair devices fixating soft tissue to bone with a bone anchor, according to another embodiment of the present invention.
Figure 11B:
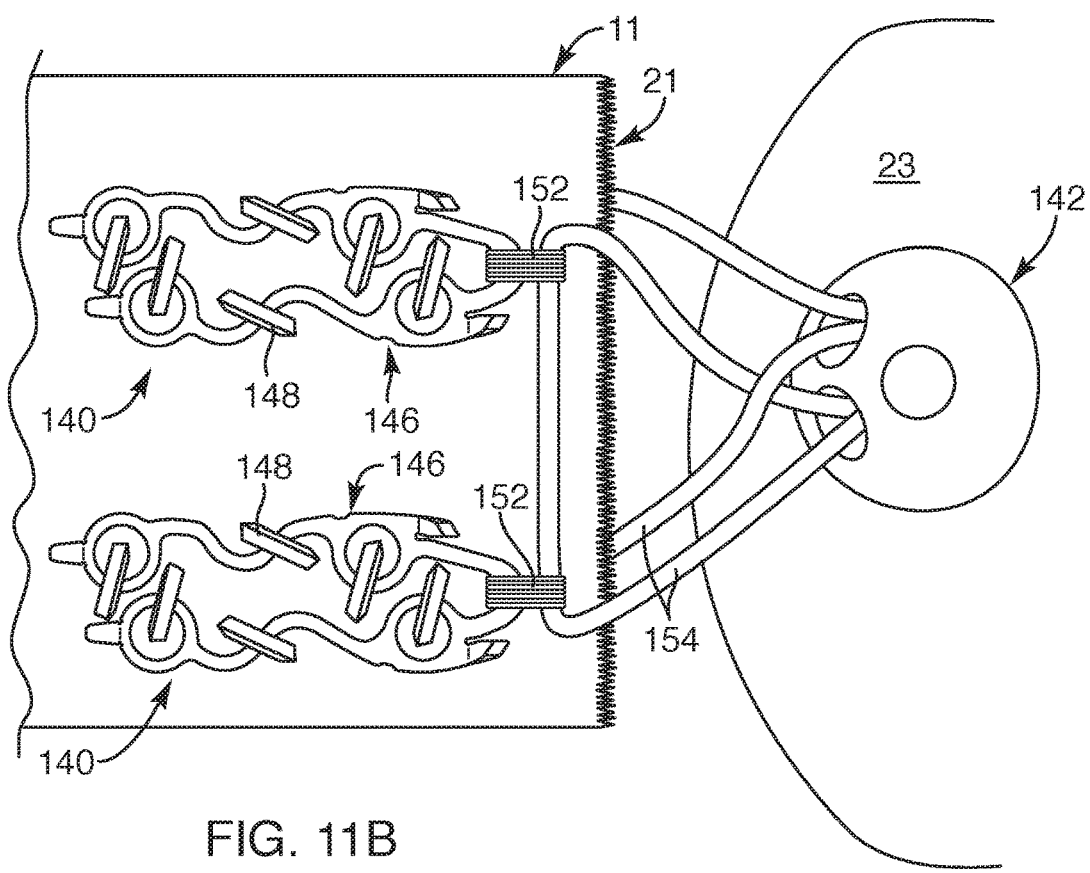
FIG. 11B is a bottom view of the one or more repair devices, depicting first capture members coupled to arms of the first anchors of the one or more repair devices fixating soft tissue to bone with the bone anchor, according to another embodiment of the present invention.
Figure 13A:
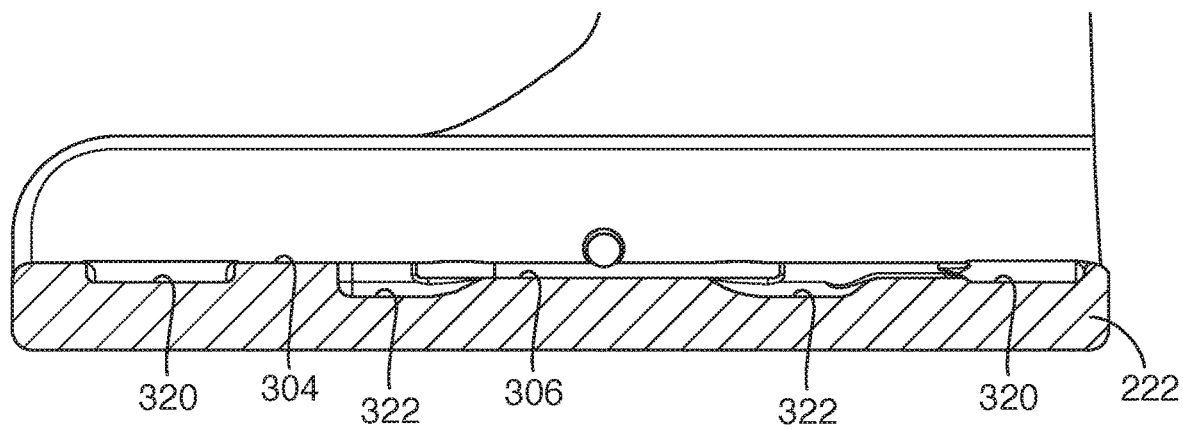
FIG. 13A is a partial cross-sectional view of the anvil taken along section A-A of FIG. 13, depicting depths of the anvil buckets defined in the anvil, according to another embodiment of the present invention.
Figure 14:
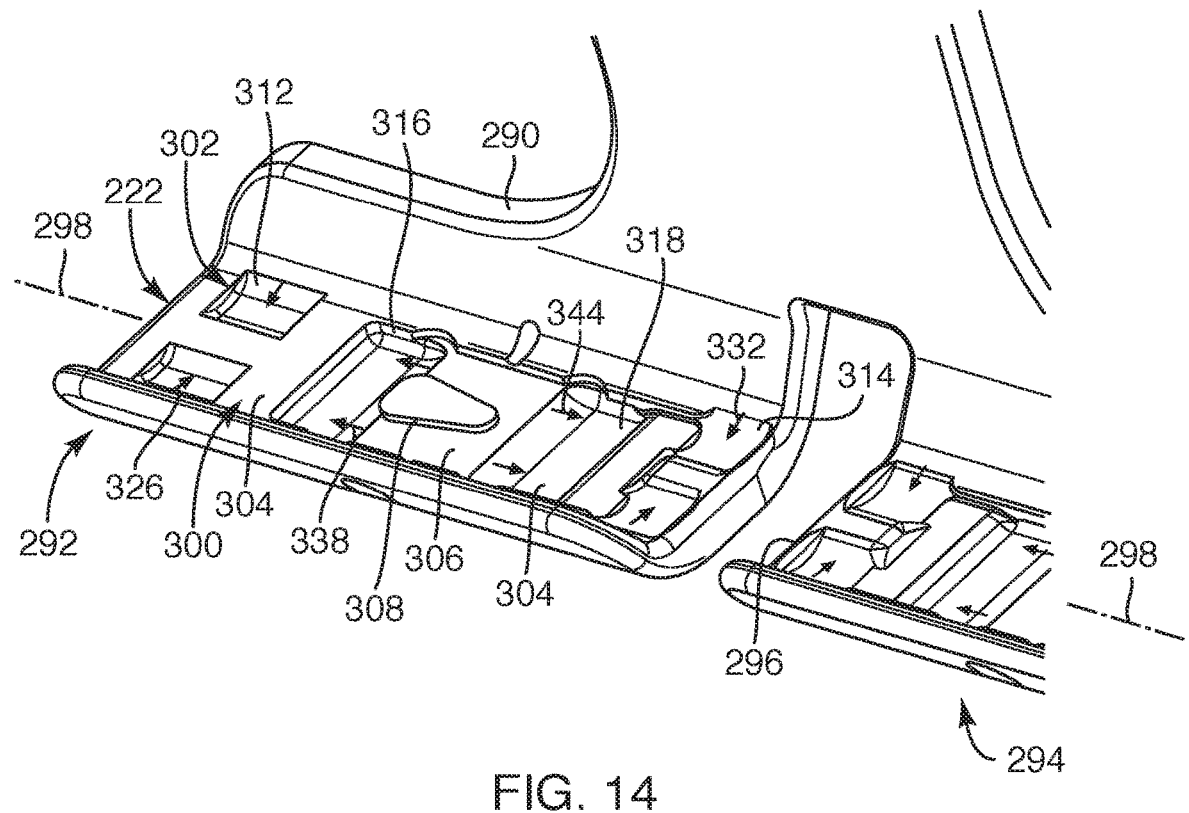
FIG. 14 is a partial perspective view of the anvil of FIG. 13, according to another embodiment of the present invention.

With reference to FIGS. 11A and 11B, a top view and a bottom view, respectively, of another embodiment of one or more repair devices 140 for fixating soft tissue 11, at a soft tissue repair site 21, to bone 23 with a bone anchor 142. The one or more repair devices 140 being similar to a first portion 130 of the previously described repair device 10 (see FIG. 8). In this embodiment, such one or more repair devices 140 may employ, for example, an anchor 144 coupled to a capture member 146 such that legs 148 of the anchor 144 extend through the soft tissue 11 and the legs 148 are formed around or curl around portions of the capture member 146, similar to previous described embodiments. Upon fixating the one or more repair devices 140 to the soft tissue 11, the one or more repair devices 140 may be coupled to the bone anchor 142. For example, a first flexible member 150 and a second flexible member 152 extending from the respective anchor 144 and the capture member 146 may be coupled to the bone anchor 142. Such may be employed by extending a bone anchor filament 154 through or around the first flexible member 150 and the second flexible member 152 and inserting and fixating the bone anchor 142 to bone 23. In this manner, one or more anchors 144 may be coupled to one or more capture members 146 to fixate soft tissue 11 to bone 23. In another embodiment, the bone anchor filament 154 may be coupled directly to one or both of the first anchors 684 as well as the bone anchor filament 694 being coupled to one or both of the capture members 146, instead of employing the first and second flexible members 150, 152.

Now with reference to FIGS. 12-16, another embodiment of a repair device 220 for fixating soft tissue ends (not shown) together is provided. This embodiment may include similar structural characteristics as the embodiment described and depicted in FIGS. 6-8 and may be employed with an anvil 222 associated with a similar delivery device to that described and depicted in FIGS. 3, 4, 5A and 5B, but the repair device 220 of this embodiment may be larger than previous embodiments and sized for fixating larger soft tissue portions. For example, this embodiment of the repair device 220 may be sized and configured to fixate to soft tissue, such as tendon in the biceps, or tendon of the posterior tibialis or anterior tibialis, or any other suitable sized tendon or soft tissue.

The repair device 220 of this embodiment, similar to previous embodiments, may include opposing structures sized and configured to couple together with soft tissue fixated therebetween. For example, the repair device 220 may include a first anchor 224 and a second anchor 226 sized and configured to couple to a first capture member 228 and a second capture member 230. Further, the first and second anchors 224, 226 may be coupled together with a first flexible member 235 and the first and second capture members 228, 230 may be coupled together with a second flexible member 234. The first and second anchors 224, 226 may be aligned along an anchor longitudinal axis 236 so as to be oriented along their respective longitudinal lengths with the first flexible member 232 therebetween. Similarly, the first and second capture members 228, 230 may be aligned along a capture member longitudinal axis 238 so as to be oriented along their respective longitudinal lengths with the second flexible member 234 therebetween. Further, the repair device 220 may also define a center lateral axis 240 extending through a lateral center of the repair device 220 such that the center lateral axis 240 extends orthogonal relative to the anchor and capture longitudinal axes 236, 238 and through both anchor and capture member longitudinal axes 236, 238. Further, such center lateral axis 240 may extend along or adjacent to severed ends of the soft tissue (not shown) to be fixated within the repair device 220. As previously set forth, each of the first and second flexible members 232, 234 may be formed with one or more filaments 242, similar to that described and depicted in previous embodiments.

Now with reference to FIGS. 12 and 15, in this embodiment, the first and second anchors 224, 226 may each include eight legs 244 extending from an anchor base 246 or base portion. In one embodiment, the anchor base 246 of each of the first and second anchors may be elongated and may extend with a flat structure or planar structure defining an upper surface 248 and an underside surface 250. The anchor base 246 may extend between a first end 252 or outer end and a second end 254 or inner end. Further, the anchor base 246 may extend between opposite first and second lateral sides 256, 258. End portions (adjacent the first and second ends 252, 254) of the anchor base 246 may define a larger width than a width of a middle portion 272 of the anchor base 246. Such end portions may include leg extensions 260 that may extend to leg pairs at the opposing first and second ends 252, 254. Such leg extensions 260 adjacent the second end 254 of the anchor base 246 may define a shoulder portion 262 sized and configured to facilitate coupling the first flexible member 232 thereto. Further, the middle portion 272 of the anchor base 246 may include two leg pairs extending from the opposite first and second lateral sides 256, 258 of the anchor base 246. With this arrangement, the first and second anchors 224, 226 may each include eight legs 244 extending from the anchor base 246.

For example, the first and second anchors 224, 226 may each include an outer leg pair 264, an inner leg pair 266, a first middle leg pair 268, and a second middle leg pair 270. The first and second middle leg pairs 268, 270 may extend from the middle portion 272 of the anchor base 246 of each of the first and second anchors 224, 226 and may be sized and configured to couple to or capture the first and second capture members 228, 230 by being formed or curling via the anvil 222 (FIG. 13) around portions of the first and second capture members 228, 230. The outer and inner leg pairs 264, 266 extending from the respective first and second ends 252, 254 of the anchor base 246 of the first and second anchors 224, 226 may be sized and configured to curl via the anvil 222 without capturing the corresponding first and second capture members 228, 230 positioned opposite the respective first and second anchors 224, 226. In this manner, some the legs 244, such as four legs, of each of the first and second anchors 224, 226 may be formed to curl around the respective first and second capture members 228, 230 and some of the legs 244, such as four legs, of each of the first and second anchors 224, 226 may be formed to curl without being coupled to the first and second capture members 228, 230.

The first and second capture members 228, 230 may each include a base 274 or base portion with spikes 276 extending therefrom. For example, the base 274 of the first and second capture members 228, 230 may be elongated and may extend with a flat structure or planar structure. The base 274 may extend between a first end 278 or outer end and a second end 280 or inner end. The first end 278 may include one or more spikes 276 extending therefrom, such as a single spike. The second end 280 may extend with a neck 282 or shoulder portion and arms 284 that extend to one or more spikes 276, such as two spikes. The neck 282 or narrow portion defined in the first and second capture members 228, 230 may facilitate coupling the first and second capture members 228, 230 with the second flexible member 234. Further, the first and second capture members 228, 230 may include structure, such as strut structure 286 or radial portions, that may extend to define recesses 288 or apertures therein, so as to define a multi-cellular structure. Such recesses 288 or apertures defined by the strut structure 286 in each of the first and second capture members 228, 230 may at least partially act as structure for at least some of the legs 244 of the first and second anchors 224, 226 to wrap or curl over as the first and second anchors 224, 226 are being compressed against the anvil 222 (FIG. 13) with tendon therebetween, similar to previous embodiments described and depicted herein.

With reference to FIGS. 12, 13, 13A, and 14, similar to previous embodiments, the anvil 222 may be integrated with a cradle member 290 that may be coupled to a delivery device (not shown). Further, the anvil 222 may include a first anvil 292 and a second anvil 294 sized and configured to correspond with the respective first and second anchors 224, 226. Further, the first anvil 292 may include structural characteristics similar to the second anvil 294 such that the first anvil 292 may generally be a mirror image of the second anvil 294. As such, description of the first anvil 292 may mirror the structure of the second anvil 294. Further, as in previous embodiments, the first anvil 292 may be separated from the second anvil 294 with a gap 296 to assist, for example, the physician to manipulate the soft tissue being positioned within the cradle member 290. In addition, the first and second anvil 292, 294 may be elongated and aligned along an anvil longitudinal axis 298, the anvil longitudinal axis 298 extending parallel with the anchor and capture member longitudinal axes 236, 238.

In one embodiment, the first and second anvil 292, 294 may include an anvil surface 300 with anvil buckets 302 defined therein, the anvil buckets 302 sized and configured to receive and manipulate the legs 1144 of the first and second anchors 1124, 1126 compressed against and through the anvil buckets 302. Further, the anvil surface 300 of the first and second anvils 292, 294 may include a first anvil surface 304 and a second anvil surface 306. The first anvil surface 304 may be at an elevation higher than the second anvil surface 306 of the anvil 222. The second anvil surface 306 of the first and second anvils 292, 294 may receive the respective first and second capture members 228, 230 of the repair device 220. Further, the second anvil surface 306 may include an upstanding wall 308 or island centrally located on the second anvil surface 306 that may correspond with structure of the first and second capture members 228, 230, such as a central aperture 310 of the first and second capture members 228, 230. Further, such upstanding wall 308 may extend to the same height as the first anvil surface 304.

The first and second anvils 292, 294 may each define outer anvil buckets 312, inner anvil buckets 314, a first middle anvil bucket 316, and a second middle anvil bucket 318. In one embodiment, the outer anvil buckets 312 may be laterally aligned (e.g., orthogonal) relative to the anvil longitudinal axis 298. Such anvil buckets 302 may define a generally rectangular periphery, as viewed from above the anvil 222. In another embodiment, the outer anvil buckets 312 may extend to a lower most first bottom surface 320 and the first and second middle anvil buckets 316, 318 may define a lower most second bottom surface 322, the first bottom surface 320 being elevated higher than the second bottom surface 322. In other words, a depth of the first and/or second middle anvil buckets 316, 318 may be greater than a depth of the outer anvil buckets 312. In another embodiment, the inner anvil buckets 314 may include a lower most bottom surface similar to a depth of the first bottom surface 320 of the outer anvil buckets 312.

Each of the outer anvil buckets 312 defined in the anvil surface 300 may extend with a radial surface 324 that at least partially defines a path, as indicated by arrow 326, for compressing and forming or curling the outer leg pairs 264 to curl inward relative to each other, as shown by arrows 328. Such radial surface 324 along the path of the outer anvil buckets 312 may define a radial axis that extends parallel with the anvil longitudinal axis 298. Similarly, the inner anvil buckets 1214 may be laterally aligned relative to the anvil longitudinal axis 1198. The inner anvil buckets 314 may be defined in the first anvil surface 304. As such, each of the inner anvil buckets 314 defined in the anvil surface 300 may include a radial surface 330 (with downward and upward slopes) to at least partially extend along and define a path, as indicated by arrows 332, for compressing and forming or curling the inner leg pairs 266 to curl inward relative to each other, as shown by arrows 334. Further, the radial surface 330 of the inner anvil buckets 314 may define a radial axis that extends parallel with the anvil longitudinal axis 298.

With respect to the first and second middle anvil buckets 316, 318 of each of the first and second anvils 292, 294, the first and second middle anvil buckets 316, 318 may each receive two legs 244, such as the respective first middle leg pairs 268 and the second middle leg pairs 270. The first and second middle anvil buckets 316, 318 may be defined in the second anvil surface 306. Further, the first and second middle anvil buckets 316, 318 may be aligned in the second anvil surface 306 along the anvil longitudinal axis 298.

The first middle anvil buckets 316 defined in the anvil surface 300 may each include a radial surface 336 (with downward and upward slopes) to define a path, as indicated by arrows 338. The radial surface 336 may define a radial axis that may be perpendicular to the anvil longitudinal axis 298. Such first middle anvil bucket 316 of the first and second anvil 292, 294 may be sized and configured to facilitate forming or curling two legs 244 therein, such as the first middle leg pair 268 of one of the first and second anchors 224, 226, so as to curl the first middle leg pair 268 in a first common direction, as shown by arrows 340, to wrap around a portion or strut structure 286 of the corresponding first and second capture members 228, 230.

Similar to the first middle anvil buckets 316, the second middle anvil buckets 318 defined in the anvil surface 300, such as the second anvil surface 306, may each include a radial surface 342 to define a path, as indicated by arrows 344, the path proceeding with downward and upward slopes. The radial surface 342 may define a radial axis that may extend perpendicular relative to the anvil longitudinal axis 298. Further, the second middle anvil bucket 318 of the first and second anvils 292, 294 may be sized and configured to facilitate forming or curling two legs 244 therein, such as the second middle leg pair 270 of one of the first and second anchors 224, 226, so as to curl the second middle leg pair 270 in a second common direction, as shown by arrows 346, to curl and wrap around a portion or strut structure 286 of the corresponding first and second capture members 228, 230. Relative to one of the first or second anchors 224, 226, the first common direction to which the first middle leg pair 268 is moved to curl may be generally opposite relative to the second common direction to which the second middle leg pair 270 is moved to curl. In this manner, the legs of the first middle leg pair 268 of the first and second anchors 224, 226 may curl in the first common direction, as indicated by arrows 340, or an outward direction generally aligned with the anvil longitudinal axis 298 and the legs of the second middle leg pair 270 of the first and second anchors 224, 226 may curl in the second common direction, as indicated by arrows 346, or an inward direction generally aligned with the anvil longitudinal axis 298. With this arrangement, the anvil 222 with its anvil buckets 302 defined therein may be sized and configured to manipulate the curl of the outer and inner leg pairs 264, 266 to curl in a generally orthogonal direction relative to the curl of the first and second middle leg pairs 268, 270. Further, the anvil buckets 302 defined in the anvil 222 may be sized and configured to curl the legs of the respective outer and inner leg pairs 264, 266 inward toward each other (e.g., in a side-ways B-configuration) while the legs of the first middle leg pair 268 curl outward toward the outer leg pair 264 and the legs of the second middle leg pair 270 curl inward toward the inner leg pair 266.

In one embodiment, one or more of the anvil buckets 302 defined in the anvil 222 may receive two legs 244 of one of the first and second anchors 224, 226 or may receive two legs 244 of both the first and second anchor 224, 226. In another embodiment, the outer and inner anvil buckets 312, 314 may be sized and configured to each receive a single leg 244 of the first and second anchors 224, 226 and the first and second middle anvil buckets 316, 318 may be sized and configured to each receive two legs 244 of the first and second anchors 224, 226. In another embodiment, two anvil buckets 302 defined in the anvil 222 may be sized and configured to each receive two legs 244 of one of the first anchor 224 or the second anchor 226 such that the two legs 244 of one anvil bucket 302 curl in a general first direction and the two legs 244 of the other anvil bucket 302 curl in a general second direction, the first direction being generally opposite to the second direction.

As depicted in FIG. 15, the one or more spikes 276 of the first and second capture members 228, 230 may extend in a canted manner. For example, the one or more spikes 276 at the first and second ends 278, 280 of the first capture member 228 may extend upward or transverse relative to the first capture member 228 so as to be canted toward the center lateral axis 240 of the first and second capture members 228, 230 or repair device 220. Similarly, the one or more spikes 276 at the first and second ends 278, 280 of the second capture member 230 may extend upward or transverse relative to the second capture member 226 so as to be canted toward the center lateral axis 240 of the first and second capture members 228, 230 or repair device 220.

FIG. 16 depicts a top view of the repair device 220. As depicted, the leg extensions 260 extend laterally outward relative to the anchor longitudinal axis 236 such that the outer and inner leg pairs 264, 266 extend from the leg extensions 260 a first lateral width 348 relative to the anchor longitudinal axis 236. The first and second middle leg pairs 268, 270 extending from the middle portion 272 of the anchor base 246 may extend a second lateral width 350 relative to the anchor longitudinal axis 236. The first lateral width 348 may be larger than the second lateral width 350. As such, as in previous embodiments, upon the legs 244 of the first and second anchors 224, 226 being compressed through soft tissue, such as tendon or ligament, the legs 244 may extend through the soft tissue at different lateral distances relative to the anchor longitudinal axis 1136 or a longitudinal axis of the soft tissue (not shown).

Figure 17:
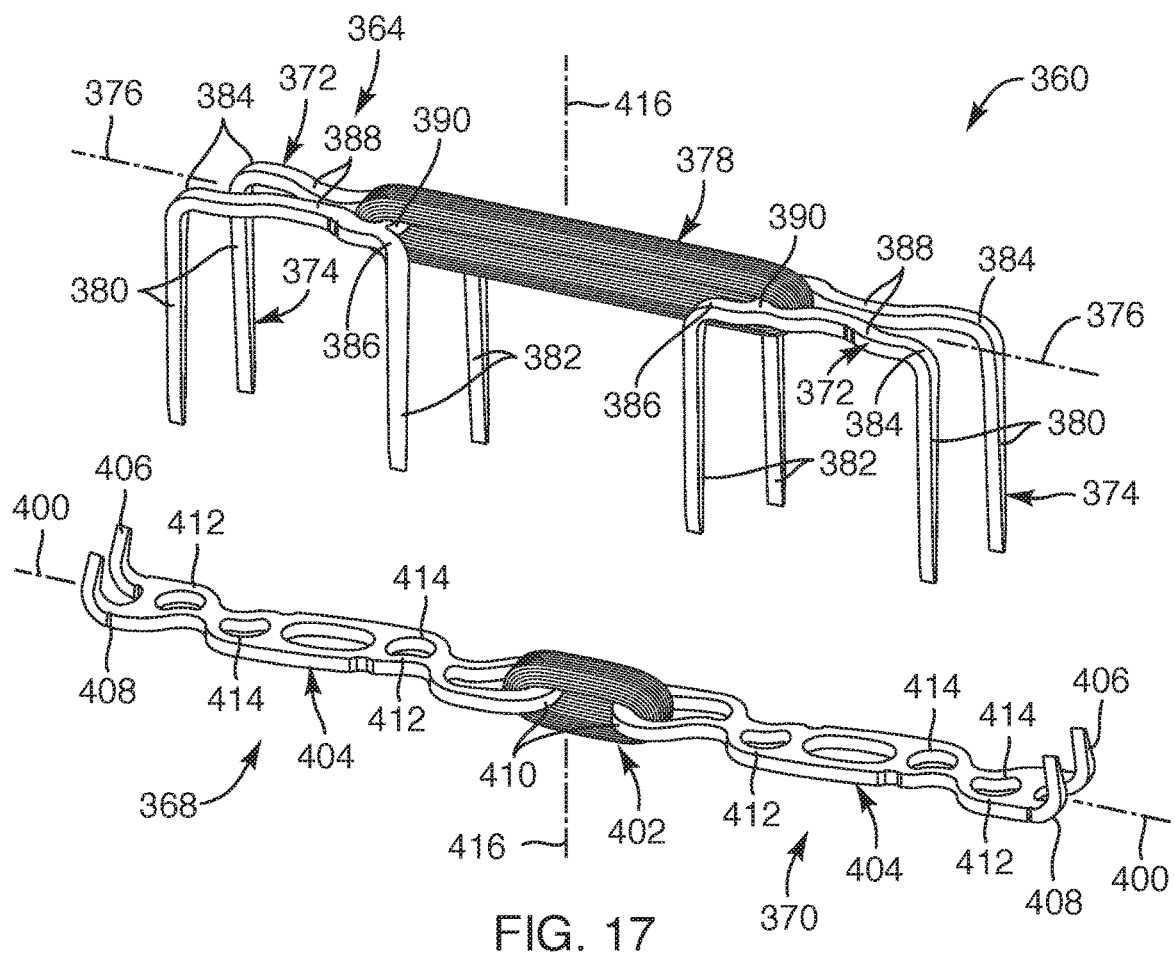
FIG. 17 is a perspective view of another embodiment of a repair device, depicting first and second anchors configured to engage with respective first and second capture members, according to the present invention.
Figure 18:
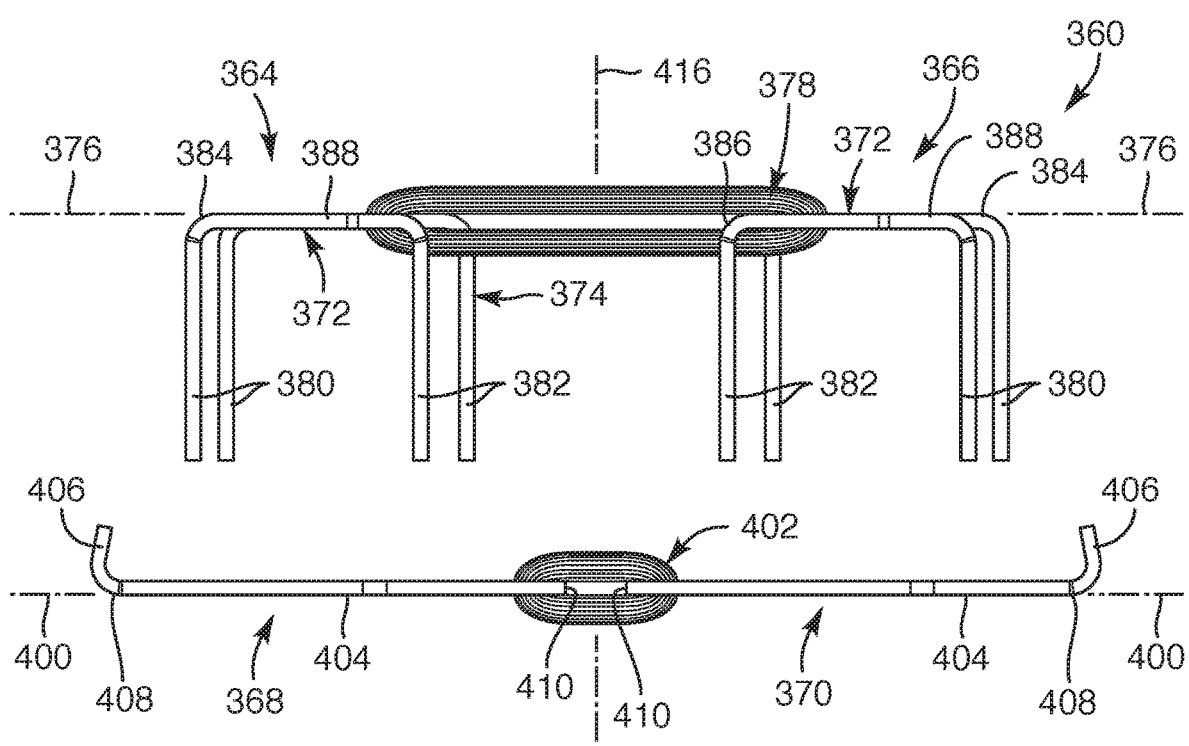
FIG. 18 is a side view of the repair device of FIG. 17, according to another embodiment of the present invention.

Now with reference to FIGS. 17 and 18, another embodiment of a repair device 360 is provided. The repair device 360 of this embodiment may be employed with an anvil 362 (FIG. 20) associated with a delivery device (not shown), such as the delivery device 12 described and depicted in FIGS. 3, 4, 5A, and 5B. The repair device 360 of this embodiment may include a narrower profile than previous embodiments, such as the repair device 360 described and depicted in FIGS. 6-8, the repair device 360 sized and configured to fixate soft tissue (not shown) together. The repair device 360 may be sized to fixate soft tissue or smaller zone two tendons, such as the small finger tendons, or extensors of the thumb or fingers, or extensor digitorum longus along the top of the foot, or any other suitable sized tendons that may correspond with the size of the repair device 360.

Similar to previous embodiments, the repair device 360 of this embodiment may include a first anchor 364 and a second anchor 366 positioned opposite of a first capture member 368 and a second capture member 370, respectively. The first and second anchors 364, 366 may each include an anchor base 372 with legs extending therefrom. The anchor base 372 of each of the first and second anchors 364, 366 may be elongated such that the anchor base 372 of the first and second anchors 364, 366 may be positioned/oriented and aligned along an anchor longitudinal axis 376 and coupled with a first flexible member 378 therebetween. Each anchor base 372 may include four legs 374 or two leg pairs, namely, an outer leg pair 380 and an inner leg pair 382. As such, the repair device 360 may include eight legs 374 for the first and second anchors 364, 366.

Further, each anchor base 372 may extend with two elongate portions 388 each extending between an outer end 384 and an inner end 386 of the two elongate portions 388. The inner leg pair 382 extending from the inner ends 386 of the two elongate portions 388 and the outer leg pair 380 extending from the outer ends 384 of the two elongate portions 388. Further, the two elongate portions 388 of each anchor base 372 may include an intermediate portion 390 extending transverse between the two elongate portions 388, the intermediate portion 390 extending adjacent the inner ends 386 of the two elongate portions 388. Such intermediate portion 390 may provide coupling structure that may be employed to couple the first and second anchors 364, 366 together with the first flexible member 378.

Figure 19:
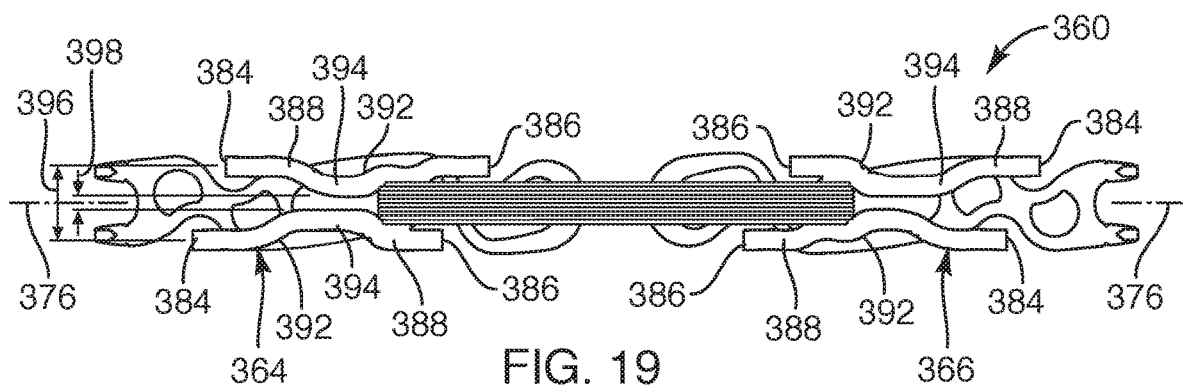
FIG. 19 is a top view of the repair device of FIG. 17, according to another embodiment of the present invention.

With respect to FIG. 19, in one embodiment, each of the two elongate portions 388 of the first and second anchors 364, 366 of the repair device 360 may extend off-set relative to each other. In another embodiment, the two elongate portions 388 may extend with one or more bends 392. In another embodiment, end portions or the outer and inner ends 384, 386 of the two elongate portions 388 may be a similar or common first distance 396 from each other and relative to the anchor longitudinal axis 376 with middle portions 394 of the two elongate portions 388 extending with the bends 392 or a curve to define a second distance 398 from each other and relative to the anchor longitudinal axis 376, the second distance 398 being smaller than the first distance 396.

Now referring again to FIGS. 17, 18, and 21, the first and second capture members 368, 370 or capture plates of the repair device 360 may be elongated and positioned along a capture member longitudinal axis 400 and may be coupled together with a second flexible member 402 therebetween. The first and second capture members 368, 370 of this embodiment may also extend with a narrower profile relative to previous embodiments so as to be sized and configured to couple to the legs 374 of the first and second anchors 364, 366. The first and second capture members 368, 370 may each include a base portion 404 and one or more spikes 406 extending upward therefrom. The base portion 404 may extend between an outer end 408 and an inner end 410 and may extend generally flat and planar. The base portion 404 may extend with strut structure 412 to define openings 414 or recesses therein. In one embodiment, the base portion 404 may extend with multiple struts so as to exhibit a multi-cellular structure.

The inner end 410 of each base portion 404 may include structure, such as strut structure 412, for coupling the first and second capture members 368, 370 together with one or more flexible filaments or the second flexible member 402. As depicted in FIG. 18, the outer ends 408 of each base portion 404 may extend to the one or more spikes 406, such as two spikes, extending upward from each base portion 404 of the first and second capture members 368, 370. The one or more spikes 406 may extend inward in a canted manner. For example, the one or more spikes 406 of the first capture member 368 may extend toward the first anchor 364 and be canted toward a center lateral axis 416 of the repair device 360 and the one or more spikes 406 of the second capture member 370 may extend toward the second anchor 366 and may be canted toward the center lateral axis 416 of the repair device 360.

Figure 20:
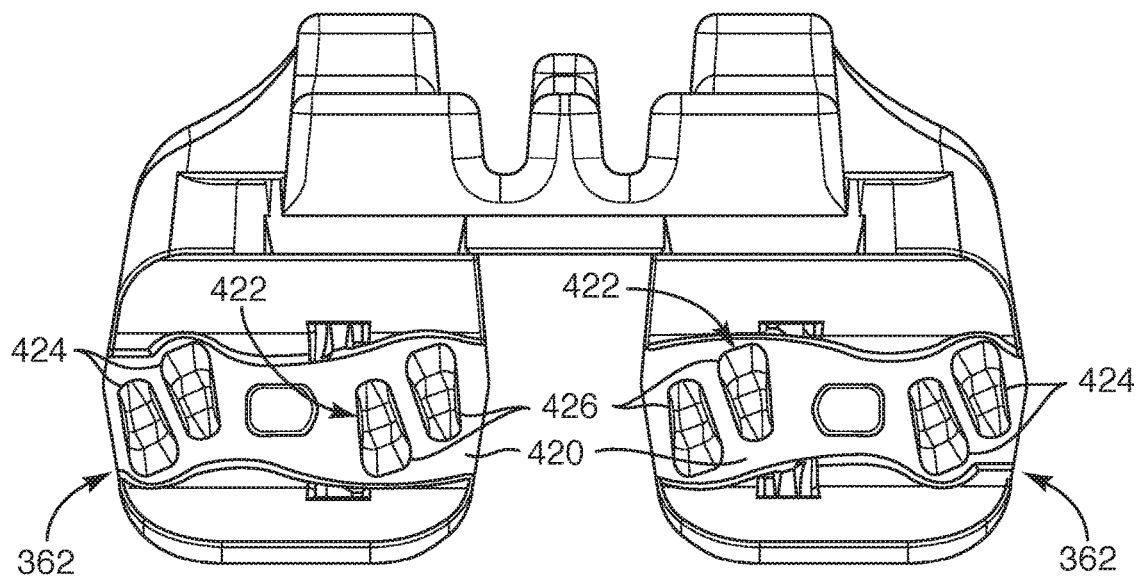
FIG. 20 is a top view of an anvil, depicting anvil buckets defined in the anvil sized for the repair device of FIG. 17, according to another embodiment of the present invention.

Now with reference to FIGS. 17 and 20, as in previous embodiments, the first and second capture members 368, 370 may be positioned on an anvil surface 420 of the anvil 362 of a delivery device (not shown), similar to the delivery device 12 described and depicted in FIGS. 3, 4, 5A and 5B. Such anvil 362 may include the anvil surface 420 with anvil buckets 422 defined therein. In this embodiment, the anvil 362 may define eight anvil buckets 422, each anvil bucket to correspond with one of the eight legs 374 of the first and second anchors 364, 366. With this arrangement, each anvil bucket 422 may be sized and configured to receive (in a compressive manner) a free end of one of the legs 374 so that the legs may be manipulated to be formed, such as in a curled configuration, to wrap around strut structure 412 of the first and second capture members 368, 370. For example, the legs 374 of the outer leg pair 380 of the first and second anchors 364, 366 may correspond with outer anvil buckets 424 and the legs 374 of the inner leg pair 382 of the first and second anchors 364, 366 may correspond with inner anvil buckets 426. In this manner, upon positioning the first and second capture members 368, 370 over the anvil surface 420, the legs 374 of the first and second anchors 364, 366 may be compressed and moved to a curled configuration to couple to the first and second capture members 368, 370, respectively, with soft tissue (not shown) positioned therebetween, similar to previous embodiments.

Figure 21:
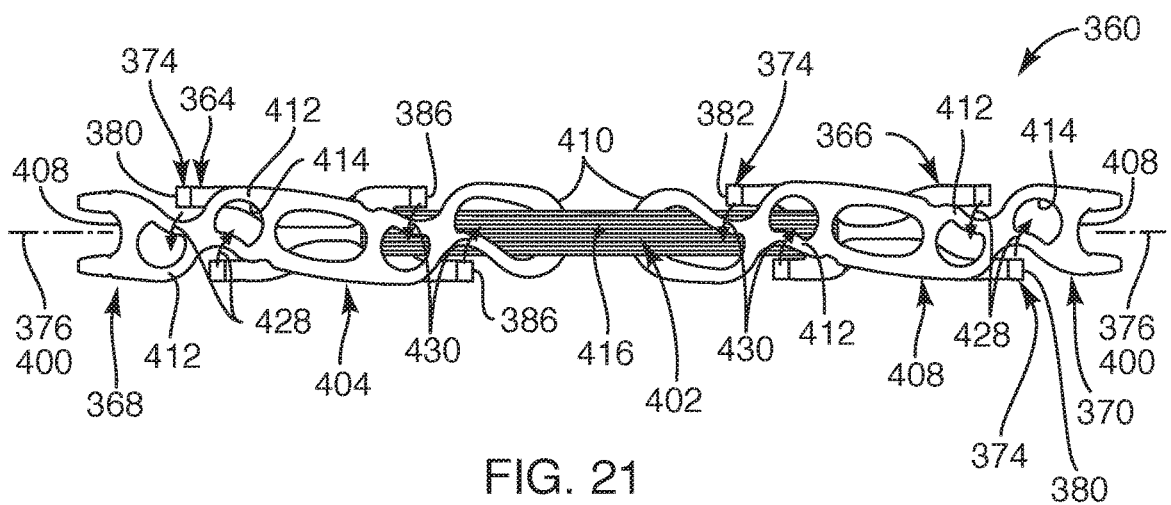
FIG. 21 is a bottom view of the repair device of FIG. 17, according to another embodiment of the present invention.

As depicted in FIGS. 19, 20 and 21, similar to previous embodiments described herein, the first and second capture members 368, 370 may include strut structure 412 sized and configured to receive the legs 374 of the first and second anchors 364, 366, respectively. For example, upon the legs 374 being simultaneously compressed against the outer and inner anvil buckets 424, 426, the legs 374 of the outer leg pair 380 of the first and second anchors 364, 366 may curl around strut structure 412 of respective first and second capture members 368, 370, as indicated by arrows 428, and the legs 374 of the inner leg pair 382 of the first and second anchors 364, 366 may curl around strut structure 412 of the first and second capture members 368, 370, as indicated by arrows 430.

Figure 22:
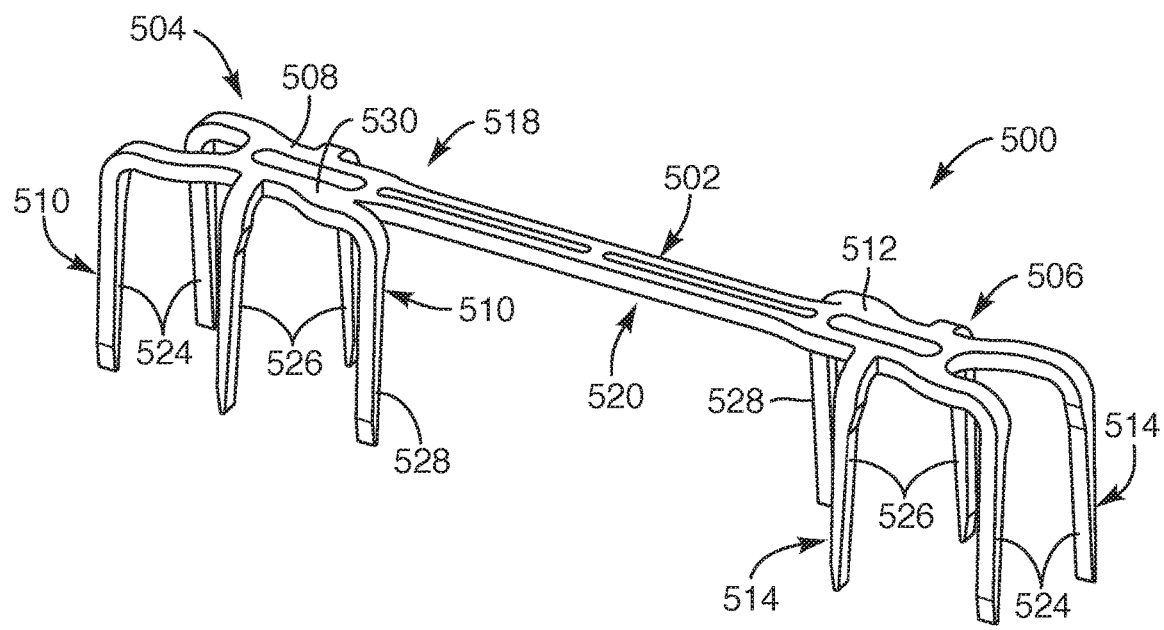
FIG. 22 is a perspective view of another embodiment of a repair device, according to the present invention.
Figure 23:
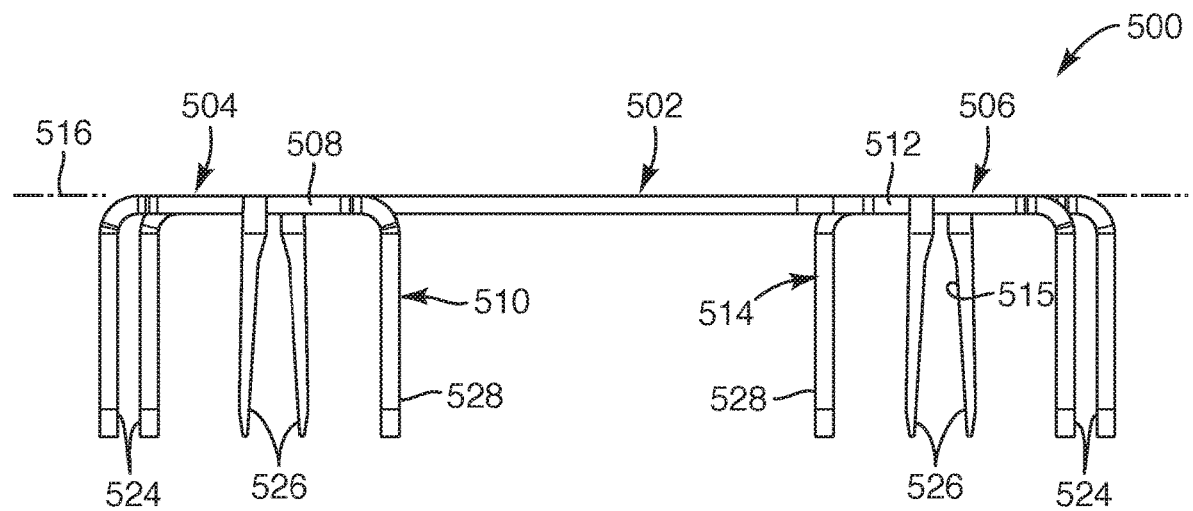
FIG. 23 is a side view of the repair device of FIG. 22, according to another embodiment of the present invention.
Figure 24:
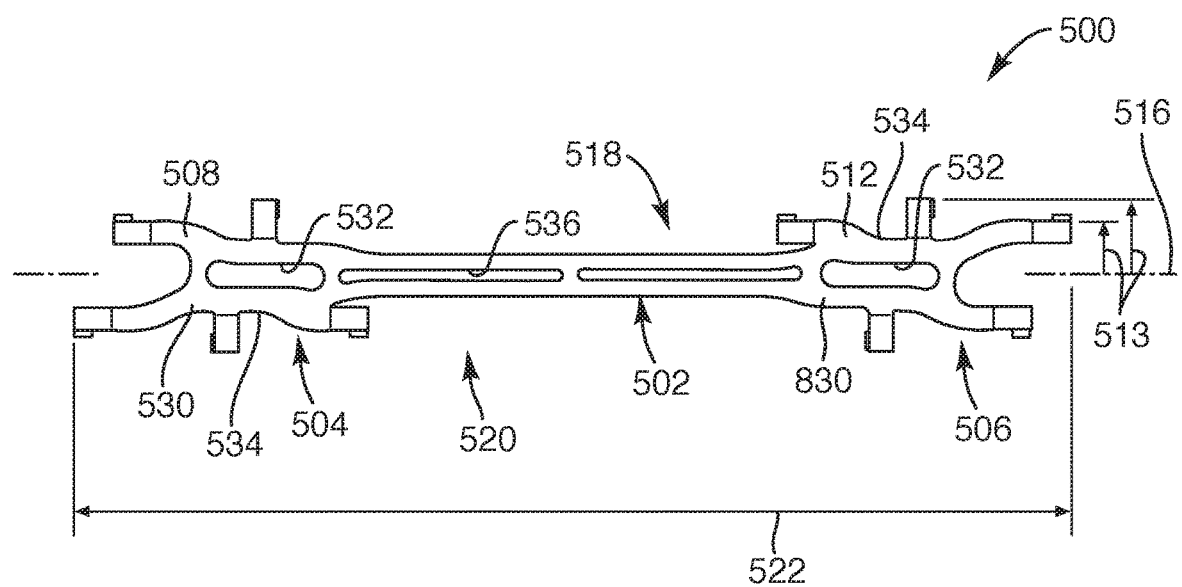
FIG. 24 is a top view of the repair device of FIG. 22, according to another embodiment of the present invention.

Now with reference to FIGS. 22-24, another embodiment of a repair device 500 is provided. The repair device 500 may be sized and configured as an anchor for fixating tendon ends together. In this embodiment, the repair device 500 may include similar structural characteristics made of similar materials and manufacturing techniques to that of previous embodiments, such as the repair device 10 of FIG. 6, except the repair device 500 may be delivered independent of the capture members of the previous embodiments such that the repair device 500 may only fixate to a tendon by virtue of its one or more anchor portions. Further, the repair device 500 of this embodiment may include an intermediate portion 502 formed integrally with the repair device 500, instead of the separately formed flexible member of previous embodiments. As such, the intermediate portion 502 may be structurally rigid and may be a similar rigidity as other portions of the repair device, such as the anchor. Also, in one embodiment, legs of the repair device 500 may include a length that is shorter than legs of previous embodiments.

For example, the repair device 500 may extend to define a first anchor portion 504 and a second anchor portion 506 with the intermediate portion 502 extending therebetween. The first anchor portion 504 may extend with a first base 508 having first legs 510 extending therefrom. Similarly, the second anchor portion 506 may extend with a second base 512 having second legs 514 extending therefrom. The first base 508 and the second base 512 may extend coplanar with the intermediate portion 502 of the repair device 500. As such, the first base 508, the second base 512, and the intermediate portion 502 may be considered as a base or base portion of the repair device 500. Further, the repair device 500 may define an elongated structure to define a longitudinal axis 516 along a length 522 of the repair device 500, the repair device 500 defining a first lateral side 518 and an oppositely positioned second lateral side 520 relative to the longitudinal axis 516.

In one embodiment, each of the first and second anchor portions 504, 506 may include five legs, of which the five legs may be defined by two outer legs 524, two middle legs 526 and one inner leg 528. The two outer and middle legs 524, 526 may extend from opposite first and second lateral sides 518, 520 of each of the first and second anchor portions 504, 506. The one inner leg 528 of the first and second anchor portions 504, 506 may extend from opposite first and second lateral sides 518, 520 of the repair device 500. The first and second legs 510, 514 of the first and second anchor portions 504, 506 may include similar structural characteristics as legs of previous embodiments described herein. For example, the first and second legs 510, 514 may each include one or more tapers 515 along a length of a given leg such that the one or more tapers 515 may be sized and configured to facilitate the legs to move to a curled configuration 538 (see FIG. 25). Further, along any one of the first and second lateral sides 518, 520, adjacent legs of the first and second legs 510, 514 may extend downward from the corresponding first and second base 508, 512 at different distances 513 from and relative to the longitudinal axis 516.

In another embodiment, the first and second anchor portions 504, 506 of the repair device 500 may each include six legs, similar to previously depicted embodiments, sized to be moved to a curled configuration for fixating to soft tissue. In another embodiment, the repair device 500 may include at least four legs extending from each of the first and second anchor portions 504, 506, sized to be moved to a curled configuration for fixating to soft tissue. In another embodiment, the first and second anchor portions 504, 506 may each include four legs, each defined by two outer legs 524 and two middle legs 526 such that the one inner leg may not be included with the repair device. In another embodiment, the repair device 500 may define eight legs sized to be moved to a curled configuration for fixating to soft tissue. In another embodiment, the repair device 500 may define ten legs sized and configured to be moved to a curled configuration for fixating to soft tissue. In still another embodiment, the repair device 500 may define twelve legs sized and configured to be moved to a curled configuration for fixating to soft tissue.

In another embodiment, the repair device 500 may define one or more apertures extending through portions of the repair device 500. For example, the first base 808 and the second base 512 may each include a flat elongated structure 530 that may define an elongated aperture 532 therein, the flat elongated structure 530 having the before-described legs extending therefrom. Such flat elongated structure 530 of the first and second base 508, 512 may define undulations 534 along a periphery thereof. Further, the intermediate portion 502 may extend with one or more elongated openings 536 defined therein.

The repair device 500 may extend as a single seamless, monolithic structure. In other words, the first anchor portion 504, the second anchor portion 506, and the intermediate portion 502 may each extend as the single seamless, monolithic structure. As such, the intermediate portion 502 may be a rigid member and a rigid coupling between the first and second anchor portions 504, 506. In another embodiment, the intermediate portion 502 may be a rigid coupling formed as a separate component, coupling the first and second anchor portions 504, 506 together. In another embodiment, similar to previous embodiments, the intermediate portion 502 may be a flexible member formed as a separate component that may be sized and configured to couple the first and second anchor portions 504, 506 together. The flexible member may be made from one or more filaments, as set forth in previous embodiments herein.

Figure 25:
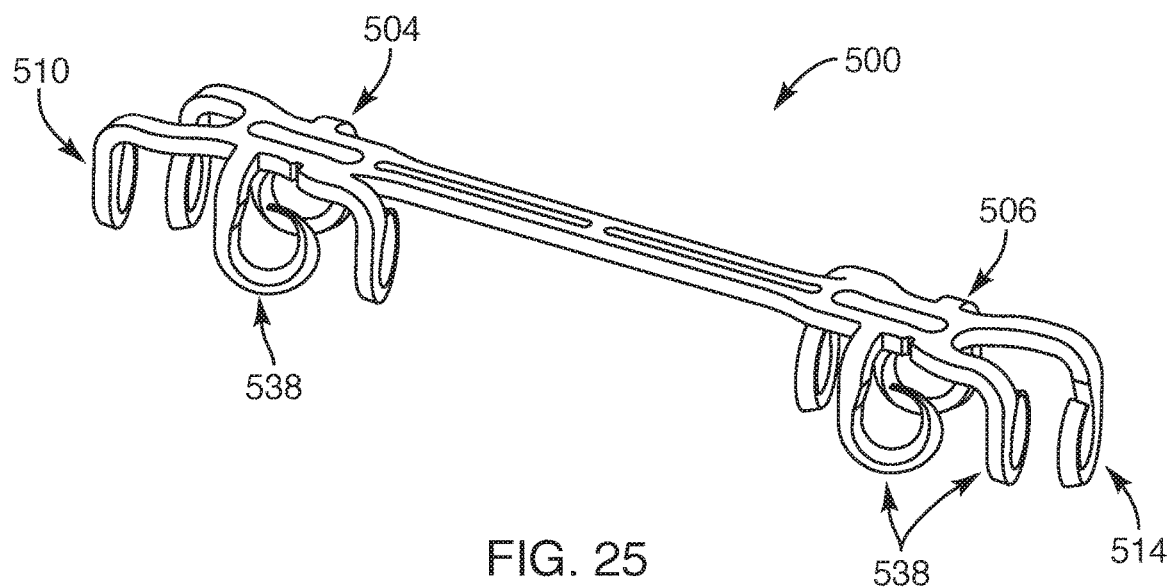
FIG. 25 is a perspective view of the repair device of FIG. 22, depicting the repair device with the legs in a formed position exhibiting a curled configuration, according to another embodiment of the present invention.

With reference to FIGS. 1, 2, 5A, 5B and 25, the repair device 500 of this embodiment may be employed with the cartridge 20 and cradle 18 of the delivery device 12 in a similar manner to that described in previous embodiments. As such, the repair device 500 may be positioned in the cartridge 20 such that the cartridge 20 may be moved toward anvil buckets 42 of the anvil 14 for fixating to soft tissue or tendon ends. In this manner, the legs of the repair device 500 may be simultaneously moved to a second position upon engaging the anvil buckets 42, moving the first and second legs 510, 514 of the first and second anchor portions 504, 506 in a curled configuration 538, as depicted in FIG. 25. The second position of the first and second legs 510, 514 of the repair device 500 may be an engaged position (being engaged with a tendon) or curled position. In this embodiment, the legs do not extend around portions of the capture members as described in previous embodiments, but rather, the first and second legs 510, 514 may be configured to fixate to a tendon or soft tissue without the additional capture members.

Figure 26A:
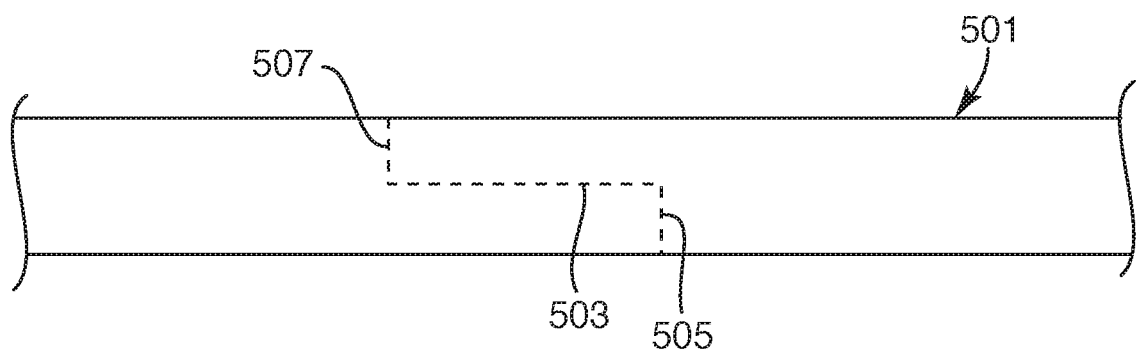
FIG. 26A is a top view of a tendon, depicting the tendon with dashed lines that indicate an incision to be made in a tendon lengthening procedure, according to another embodiment of the present invention.
Figure 26B:
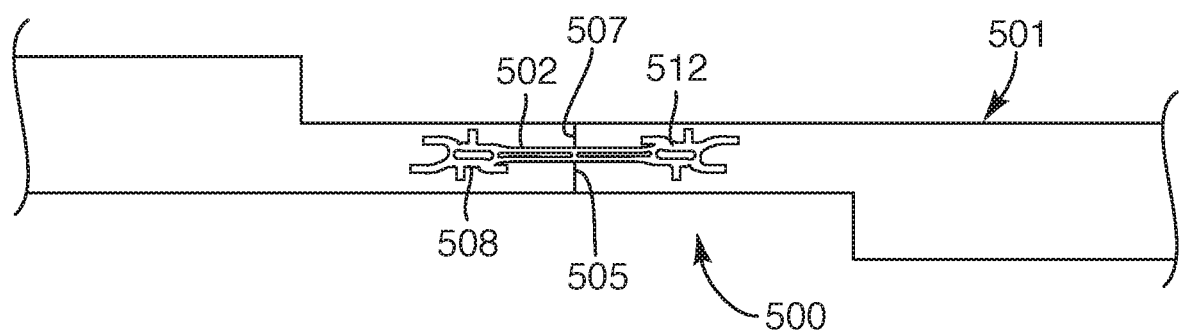
FIG. 26B is a top view of the repair device of FIG. 25, depicting the repair device coupling tendon ends of a tendon in a tendon lengthening procedure, according to another embodiment of the present invention.

With respect to FIGS. 26A and 26B, as previously set forth, the repair device 500 of this embodiment may be employed for fixating to a tendon 501 or soft tissue. In one embodiment, the repair device 500 may be utilized to facilitate a tendon lengthening procedure to treat, for example, hammer toe or any other case where tendon lengthening may be desired. As depicted in FIG. 26A, a tendon 501 that may be desired for lengthening may be cut along dashed lines 503 to perform a "z tenotomy" technique, for example. In such technique, the lateral portions of the dashed lines 503, once cut, may become a first tendon end 505 and a second tendon end 507. Upon cutting the tendon 501 along the dashed lines 503, as depicted in FIG. 26B, the first tendon end 505 may be positioned to abut the second tendon end 507. It may be desired to place a couple of sutures through the first and second tendon ends 505, 507 to maintain contact therebetween. As previously set forth, the first and second tendon ends 505, 507 may be positioned within an upper surface of an anvil 14 of a delivery device 12, similar to that depicted and described in previous embodiments, such as in FIGS. 2 and 5B. The repair device 500, being positioned within a cartridge 20, may then be deployed therefrom such that the first and second legs 510, 514 (FIG. 22) engage anvil buckets 42 so that the repair device 500 may be fixated to the tendon 501 with the intermediate portion 502 extending over the first and second tendon ends 505, 507.

Figure 27:
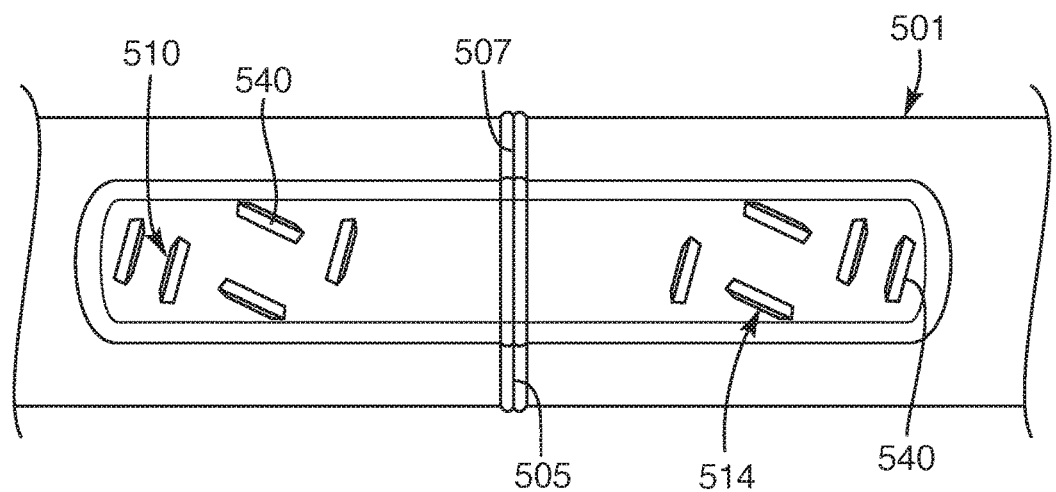
FIG. 27 is a bottom view of exposed portions of the repair device coupled to a tendon, according to another embodiment of the present invention.

As depicted in FIGS. 25, 26B and 27, the first and second legs 510, 514 of the repair device 500 extend through the tendon 501 and may be formed to curl with the curled configuration 538 back into the tendon 501. With the repair device 500 fixated to the tendon, a portion of the first and second legs 510, 514 in the curled configuration 538 (FIG. 25) may be exposed to exhibit exposed portions 540, as depicted in FIG. 27, on one side of the tendon 501 or soft tissue. At the opposite side of the tendon 501 or soft tissue, the first base 508 and second base 512 and intermediate portion 502 of the repair device 500 may be exposed, as depicted in FIG. 26B. In this manner, the repair device 500 may fixate to a tendon 501 for the purpose of tendon lengthening upon the repair device 500 being moved to the second position via the anvil 14 (FIG. 2). It should be noted that the repair device 500 of this embodiment may be employed for approximating and fixating tendon ends together (in a non-tendon lengthening procedure), or may be employed for fixating soft tissue at a soft tissue repair site, such as tendon to ligament or ligament to ligament, or tendon/ligament to bone fixation, as set forth in previous embodiments herein.

Figure 26C:
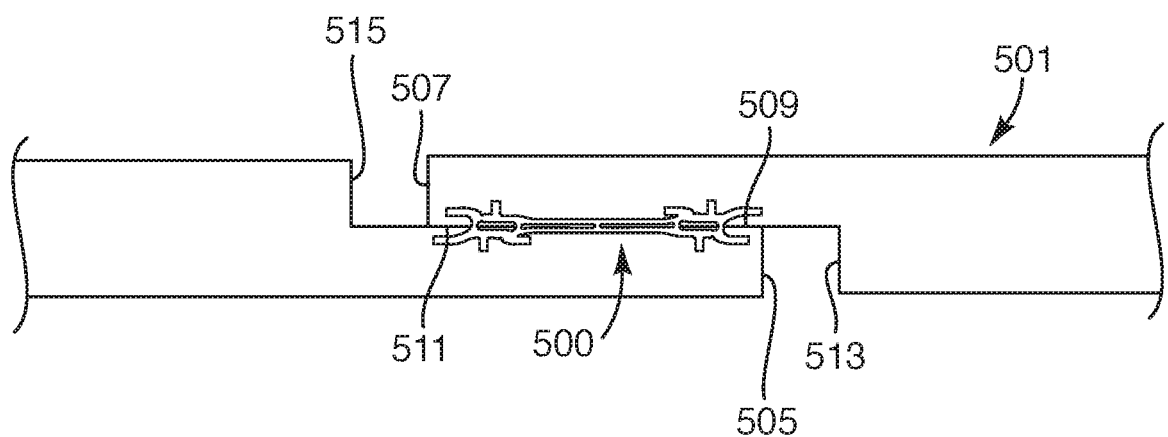
FIG. 26C is a top view of the repair device of FIG. 25, depicting the repair device coupling lateral sides of a tendon in a tendon lengthening procedure, according to another embodiment of the present invention.

With respect to FIG. 26C, another embodiment for tendon lengthening with the repair device 500 is provided. This embodiment employs a slightly different technique for tendon lengthening, but may be employed with the repair device 500 in a similar manner as described in the previous embodiment. For example, the tendon 501 may be cut similarly along dashed lines 503, as depicted in FIG. 26A. Instead of positioning first and second tendon ends 505, 507 against each other, first and second lateral sides 509, 511 that are adjacent the first and second tendon ends 505, 507 are coupled together with the repair device 500. This technique of tendon lengthening may leave first and second gaps 513, 515 in the coupled tendon 801. In this manner, the repair device 500 may be employed for treating and fixating a tendon in a tendon lengthening procedure with the delivery device 12 (FIG. 3) as described herein.

Figure 28:
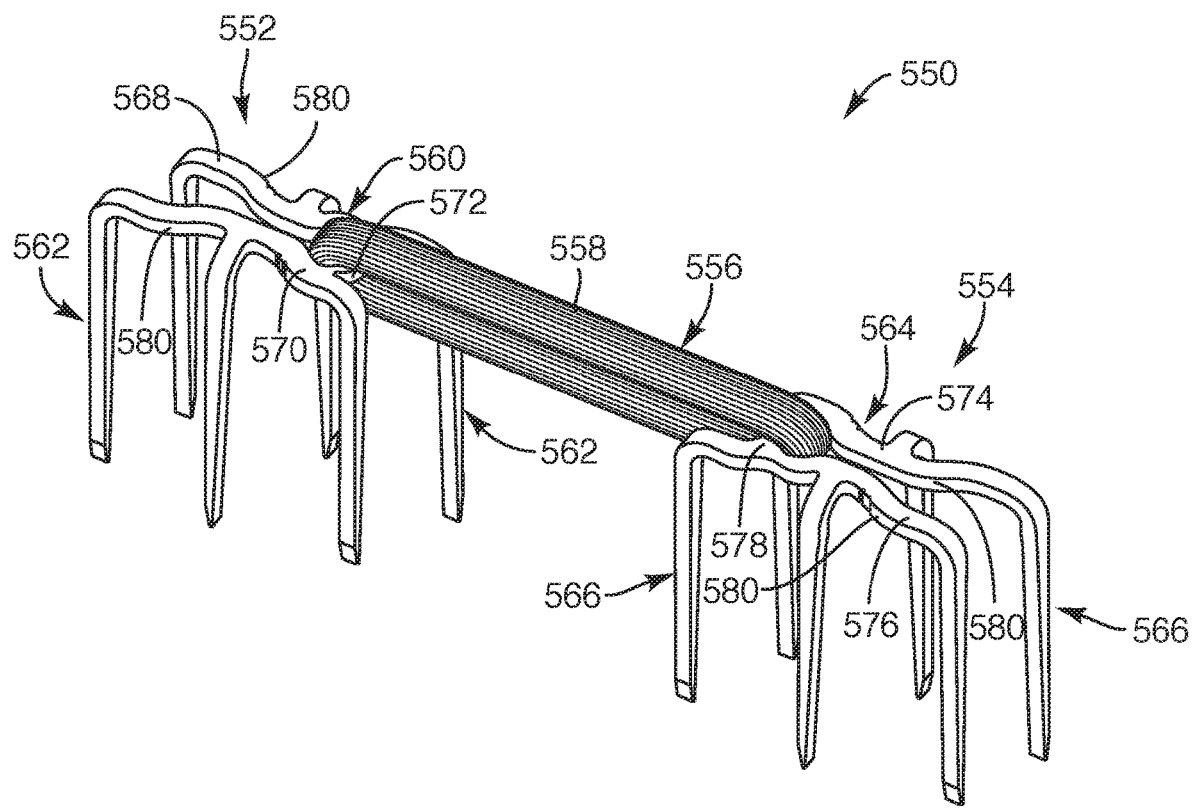
FIG. 28 is a perspective view of another embodiment of a repair device for fixating tendon portions or ends in a tendon lengthening procedure, according to the present invention.

Now with reference to FIG. 28, another embodiment of a repair device 550 is provided. The repair device 550 of this embodiment is similar to the previous embodiment, except anchor portions may be coupled with a flexible member. This embodiment may also be similar to the anchor portions of the repair device depicted in FIGS. 6-7. As such, the description set forth herein relative to the anchor portions and intermediate portion or flexible member relative to FIGS. 6-7 as well as like anchor portion embodiments may be applicable relative to this embodiment of the repair device 550. As in the previous embodiment, the repair device 550 of this embodiment may be employed without capture members for fixating to a tendon.

In this embodiment, the repair device 550 may include a first anchor portion 552 and a second anchor portion 554 with an intermediate portion 556 extending therebetween. As set forth, the intermediate portion 556 may be the flexible member 558. The flexible member 558 may be formed with one or more filaments wrapped around portions of the first and second anchor portions 552, 554. The first anchor portion 552 may include a first base 560 with first legs 562 extending therefrom. The second anchor portion 554 may include a second base 564 with second legs 566 extending therefrom. The first base 560 may include a first elongate portion 568 and a second elongate portion 570 with a transverse portion 572 therebetween. Likewise, the second base 564 may include a third elongate portion 574 and a fourth elongate portion 576 with a transverse portion 578 therebetween. Each of first, second, third, and fourth elongate portions 568, 570, 574, 576 may include at least two legs extending therefrom and, in one embodiment, three legs extending from each elongate portion, as depicted. Further, each of the first, second, third, and fourth elongate portions 568, 570, 574, 576 may extend in a wave configuration or with a radius so as to define undulations 580 along their respective length. The intermediate portion 556 may extend from and between the transverse portions 572, 578 of each of the first and second anchor portions 552, 554.

In one embodiment, the first and second anchor portions 552, 554 may each include six legs, totaling twelve legs for the repair device 550. In another embodiment, the first and second anchor portions 552, 554 may each include four legs, totaling at least eight legs for the repair device 550.

With reference to FIGS. 2, 5B, and 28, the repair device 550 with its first and second anchor portions 552, 554 and intermediate portion 556 may be positioned within, for example, the cartridge 20 of the delivery device 12 with tendon ends positioned over the upper surface 40 of the anvil 14 for deploying the repair device 550 into the tendon so that anvil buckets 42 defined in the upper surface 40 may be shaped to cause the first and second legs 562, 566 to be forced to move to a curled configuration to fixate tendon ends together, similar to that described in previous embodiments. In this manner, the repair device 550 may fixate tendon ends or soft tissue together.

The various repair device embodiments or other embodiments disclosed herein may be applied to any one of various soft tissue to soft tissue repairs as well as soft tissue to bone repairs. For example, the various repair device embodiments may be employed for flexor tendon repairs, patellar tendon repairs, Achilles tendon repairs, quadriceps tendon repairs, and/or bicep tendon repairs, or any other tendon, ligament, and tendon/ligament to bone repairs. As such, the repair device may be appropriately sized for proper fixation to the different sized or types of soft tissue.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:

1. A repair device system for coupling to soft tissue, comprising:
 a delivery device having a handle and a push rod defining a longitudinal axis, the push rod configured to linearly move along the longitudinal axis;
 an implant delivery member configured to be removably coupled to the delivery device, the implant delivery member including a cartridge and an anvil, the cartridge linearly moveable relative to the anvil to facilitate moving one end of the cartridge to be positioned adjacent the soft tissue positioned over the anvil, the anvil having an upper surface defining anvil buckets therein such that the upper surface defines a raised structure extending above the upper surface; and
 a repair device including an anchor and a capture member, the anchor having a base with at least four legs extending from the base such that the anchor is held within the cartridge, the capture member positioned on the anvil against the raised structure such that the raised structure assists in positioning the capture member on the anvil, wherein, upon movement of the push rod with the delivery device, the push rod is configured to move the anchor from the cartridge so that the base of the anchor moves in a direction corresponding with the linear movement of the push rod along the longitudinal axis to move the at least four legs against the anvil such that the at least four legs move from a linear position to a formed position;
 wherein the capture member is configured to be coupled to the anchor with the at least four legs in the formed position such that the at least four legs are formed around structure of the capture member.

2. The repair device system of claim 1, wherein the repair device is configured to couple to soft tissue with the anchor and the capture member on opposing sides of the soft tissue.

3. The repair device system of claim 1, wherein the base of the anchor comprises an elongated structure defining a base axis and the anvil being elongated to define an anvil axis, the base axis extending substantially parallel relative to the anvil axis.

4. The repair device system of claim 1, wherein the anvil is elongated to define an anvil axis, the anvil axis extending substantially perpendicular relative to the longitudinal axis of the push rod.

5. The repair device system of claim 1, wherein, upon the implant delivery member being coupled to the delivery device, the push rod is configured to couple to the cartridge.

6. The repair device system of claim 1, wherein the delivery device comprises a worm drive configured to be rotated by a thumb wheel, the worm drive configured to couple to a base portion of the implant delivery member.

7. The repair device system of claim 1, wherein, upon the implant delivery member being coupled to the delivery device, the at least four legs of the anchor held in the cartridge extend substantially parallel with the longitudinal axis of the push rod.

8. A repair device system configured to couple to soft tissue, the repair device system comprising:
   an anvil having an upper surface defining anvil buckets therein, the upper surface including a raised structure extending upward from the upper surface;
   at least one anchor operatively coupled to the anvil, the at least one anchor having a base with at least four legs extending from the base, the at least four legs configured to be compressed against the anvil buckets to move the at least four legs to a formed position; and
   at least one capture member, the at least one capture member extending with a rigid flat structure with a capture member surface facing and positionable over the upper surface of the anvil and adjacent the anvil buckets such that the rigid flat structure is positioned against the raised structure of the anvil;
   wherein, upon the at least four legs being compressed into the anvil buckets of the anvil, the at least four legs are formed around the capture member surface and wrap around a periphery of the rigid flat structure of the at least one capture member so that the at least one anchor is coupled to the at least one capture member with the soft tissue therebetween.

9. The repair device system of claim 8, wherein the at least one anchor comprises a first anchor and a second anchor, the first anchor coupled to the second anchor with a flexible member.

10. The repair device system of claim 9, wherein the flexible member comprises one or more filaments.

11. The repair device system of claim 8, wherein at least one of the anvil buckets is sized and configured to correspond with two legs of the at least four legs.

12. The repair device system of claim 8, wherein the least one capture member is configured to be positioned on the upper surface of the anvil so that some of the at least four legs couple to the at least one capture member, upon the at least four legs being compressed against the anvil buckets.

13. The repair device system of claim 8, wherein the upper surface of the anvil comprises a first surface and a second surface each with the anvil buckets defined therein, the first surface being elevated higher than the second surface.

14. The repair device system of claim 8, wherein the anvil buckets defined in the upper surface of the anvil define at least two depths in the upper surface.

15. The repair device system of claim 8, further comprising a bone anchor configured to be coupled to the at least one anchor with a flexible member.

16. The repair device system of claim 8, wherein the raised structure is positioned on the anvil to engage an inner surface of the rigid flat structure.

17. A repair device system configured to couple to soft tissue, the repair device system comprising:
   an anvil having an upper surface defining anvil buckets therein, the upper surface including a raised structure extending upward from the upper surface;
   a capture portion having a rigid flat structure extending with oppositely facing first and second surfaces with a periphery defined between the first and second surfaces, the capture portion configured to be temporarily positioned directly onto the upper surface of the anvil and against the raised structure; and
   an anchor portion having a base with multiple legs extending therefrom, the multiple legs configured to move from a linear position to a formed position such that, in the linear position, the anchor portion is configured to be positioned so that the legs extend toward the first surface of the capture portion with the capture portion positioned against the raised structure of the anvil and, in the formed position, the multiple legs wrap around the second surface and the periphery of the rigid flat structure of the capture portion.

18. The repair device system of claim 17, further comprising a flexible member coupled to at least one of the capture portion and the anchor portion, the flexible member configured to be coupled to a bone anchor.

19. The repair device system of claim 17, wherein the anchor portion comprises a first anchor and a second anchor with a flexible member coupled therebetween.

20. The repair device system of claim 17, wherein the capture portion extends with multiple apertures therein.

21. The repair device system of claim 17, wherein the capture portion and the anchor portion extends with elongated structures.

22. The repair device system of claim 17, wherein the multiple legs of the anchor portion are sized and configured to couple to radially extending portions of the capture portion.

23. The repair device system of claim 17, wherein the raised structure is positioned on the anvil to engage an inner surface of the rigid flat structure.

* * * * *